(12) United States Patent
Teter et al.

(10) Patent No.: US 9,045,748 B2
(45) Date of Patent: Jun. 2, 2015

(54) METHODS FOR TRANSFORMING AND EXPRESSION SCREENING OF FILAMENTOUS FUNGAL CELLS WITH A DNA LIBRARY

(75) Inventors: Sarah Teter, Menlo Park, CA (US); Michael Lamsa, Davis, CA (US); Joel Cherry, Davis, CA (US); Connie Ward, Hamilton, MT (US)

(73) Assignee: Novozymes, Inc., Davis, CA (US)

( * ) Notice: Subject to any disclaimer, the term of this patent is extended or adjusted under 35 U.S.C. 154(b) by 334 days.

(21) Appl. No.: 11/140,150

(22) Filed: May 26, 2005

(65) Prior Publication Data

US 2006/0172379 A1 Aug. 3, 2006

Related U.S. Application Data

(60) Provisional application No. 60/575,600, filed on May 27, 2004.

(51) Int. Cl.
*C12N 15/10* (2006.01)
*C12N 15/80* (2006.01)
*C40B 40/02* (2006.01)

(52) U.S. Cl.
CPC ........ *C12N 15/1037* (2013.01); *C12N 15/1086* (2013.01); *C12N 15/80* (2013.01); *C40B 40/02* (2013.01)

(58) Field of Classification Search
None
See application file for complete search history.

(56) References Cited

U.S. PATENT DOCUMENTS

| | | | |
|---|---|---|---|
| 4,816,405 A | 3/1989 | Timberlake et al. | |
| 5,578,463 A * | 11/1996 | Berka et al. | 435/69.1 |
| 6,309,883 B1 | 10/2001 | Minshull et al. | |
| 6,703,200 B1 | 3/2004 | Hamer et al. | |
| 7,122,330 B2 * | 10/2006 | Emalfarb et al. | 435/7.31 |
| 2003/0162218 A1 * | 8/2003 | Emalfarb et al. | 435/7.1 |

FOREIGN PATENT DOCUMENTS

| | | |
|---|---|---|
| WO | WO99/32617 | 7/1999 |
| WO | WO 00/24883 | 5/2000 |

OTHER PUBLICATIONS

Kondo et al. Plasmid Transformation of *Streptococcus lactis* Protoplasts: Optimization and Use in Molecular Cloning. Appl. and Envtl. Microbiol. 48(2): 252-259, 1984.*

Lamsa et al., "Mutation and screening to increase chymosin yield in a genetically-engineered strain of *Aspergillus awamori*", Journal of Industrial Microbiology, 1990, v. 5, p. 229-238.

Lueking et al., "A system for dual protein expression in *Pichia pastoris* and *Escherichia coil*," Protein Expression and Purification. Academic Press, 2000, v.20, p. 372-378.

Chambers et al., "High-throughput screening for soluble recombinant expressed kinases in *Escherichia coli* and insect cells," 2004, v.36, p. 40-47.

* cited by examiner

*Primary Examiner* — Michele K Joike
(74) *Attorney, Agent, or Firm* — Robert L. Starnes

(57) ABSTRACT

The present invention relates to methods for expression screening of filamentous fungal transformants, comprising: (a) isolating single colony transformants of a DNA library introduced into *E. coli*; (b) preparing DNA from each of the single colony *E. coli* transformants; (c) introducing a sample of each of the DNA preparations of step (b) into separate suspensions of protoplasts of a filamentous fungus to obtain transformants thereof, wherein each transformant contains one or more copies of an individual polynucleotide from the DNA library; (d) growing the individual filamentous fungal transformants of step (c) on selective growth medium, thereby permitting growth of the filamentous fungal transformants, while suppressing growth of untransformed filamentous fungi; and (e) measuring activity or a property of each polypeptide encoded by the individual polynucleotides. The present invention also relates to isolated polynucleotides encoding polypeptides of interest obtained by such methods, to nucleic acid constructs, expression vectors, and recombinant host cells comprising the isolated polynucleotides, and to methods of producing the polypeptides encoded by the isolated polynucleotides.

14 Claims, 6 Drawing Sheets

SEQUENCE LISTING

```
<160> NUMBER OF SEQ ID NOS: 30

<210> SEQ ID NO 1
<211> LENGTH: 20
<212> TYPE: DNA
<213> ORGANISM: Escherichia coli

<400> SEQUENCE: 1
taatacgact cactataggg                                              20

<210> SEQ ID NO 2
<211> LENGTH: 1545
<212> TYPE: DNA
<213> ORGANISM: Trichoderma reesei
<220> FEATURE:
<221> NAME/KEY: CDS
<222> LOCATION: (1)..(1539)
<220> FEATURE:
<221> NAME/KEY: sig_peptide
<222> LOCATION: (1)..(51)
<220> FEATURE:
<221> NAME/KEY: mat_peptide
<222> LOCATION: (52)..()

<400> SEQUENCE: 2 atg tat cgg aag ttg gcc gtc atc tcg gcc ttc ttg gcc aca gct cgt      48
Met Tyr Arg Lys Leu Ala Val Ile Ser Ala Phe Leu Ala Thr Ala Arg
        -15                 -10                  -5 gct cag tcg gcc tgc act ctc caa tcg gag act cac ccg cct ctg aca      96
Ala Gln Ser Ala Cys Thr Leu Gln Ser Glu Thr His Pro Pro Leu Thr
 -1   1               5                  10                  15 tgg cag aaa tgc tcg tct ggt ggc acg tgc act caa cag aca ggc tcc     144
Trp Gln Lys Cys Ser Ser Gly Gly Thr Cys Thr Gln Gln Thr Gly Ser
                 20                  25                  30 gtg gtc atc gac gcc aac tgg cgc tgg act cac gct acg aac agc agc     192
Val Val Ile Asp Ala Asn Trp Arg Trp Thr His Ala Thr Asn Ser Ser
             35                  40                  45 acg aac tgc tac gat ggc aac act tgg agc tcg acc cta tgt cct gac     240
Thr Asn Cys Tyr Asp Gly Asn Thr Trp Ser Ser Thr Leu Cys Pro Asp
         50                  55                  60 aac gag acc tgc gcg aag aac tgc tgt ctg gac ggt gcc gcc tac gcg     288
Asn Glu Thr Cys Ala Lys Asn Cys Cys Leu Asp Gly Ala Ala Tyr Ala
     65                  70                  75 tcc acg tac gga gtt acc acg agc ggt aac agc ctc tcc att ggc ttt     336
Ser Thr Tyr Gly Val Thr Thr Ser Gly Asn Ser Leu Ser Ile Gly Phe
 80                  85                  90                  95 gtc acc cag tct gcg cag aag aac gtt ggc gct cgc ctt tac ctt atg     384
Val Thr Gln Ser Ala Gln Lys Asn Val Gly Ala Arg Leu Tyr Leu Met
                100                 105                 110 gcg agc gac acg acc tac cag gaa ttc acc ctg ctt ggc aac gag ttc     432
Ala Ser Asp Thr Thr Tyr Gln Glu Phe Thr Leu Leu Gly Asn Glu Phe
            115                 120                 125 tct ttc gat gtt gat gtt tcg cag ctg ccg tgc ggc ttg aac gga gct    480
Ser Phe Asp Val Asp Val Ser Gln Leu Pro Cys Gly Leu Asn Gly Ala
```

-continued

|     |     |     | 130 |     |     |     | 135 |     |     |     | 140 |     |     |     |      |
|---|---|---|---|---|---|---|---|---|---|---|---|---|---|---|---|
| ctc | tac | ttc | gtg | tcc | atg | gac | gcg | gat | ggt | ggc | gtg | agc | aag | tat ccc | 528 |
| Leu | Tyr | Phe | Val | Ser | Met | Asp | Ala | Asp | Gly | Gly | Val | Ser | Lys | Tyr Pro |  |
|     |     | 145 |     |     |     |     | 150 |     |     |     |     | 155 |     |         |  |

| acc | aac | acc | gct | ggc | gcc | aag | tac | ggc | acg | ggg | tac | tgt | gac | agc cag | 576 |
|---|---|---|---|---|---|---|---|---|---|---|---|---|---|---|---|
| Thr | Asn | Thr | Ala | Gly | Ala | Lys | Tyr | Gly | Thr | Gly | Tyr | Cys | Asp | Ser Gln |  |
| 160 |     |     |     |     | 165 |     |     |     |     | 170 |     |     |     | 175 |  |

| tgt | ccc | cgc | gat | ctg | aag | ttc | atc | aat | ggc | cag | gcc | aac | gtt | gag ggc | 624 |
|---|---|---|---|---|---|---|---|---|---|---|---|---|---|---|---|
| Cys | Pro | Arg | Asp | Leu | Lys | Phe | Ile | Asn | Gly | Gln | Ala | Asn | Val | Glu Gly |  |
|     |     |     | 180 |     |     |     |     | 185 |     |     |     |     | 190 |         |  |

| tgg | gag | ccg | tca | tcc | aac | aac | gcg | aac | acg | ggc | att | gga | gga | cac gga | 672 |
|---|---|---|---|---|---|---|---|---|---|---|---|---|---|---|---|
| Trp | Glu | Pro | Ser | Ser | Asn | Asn | Ala | Asn | Thr | Gly | Ile | Gly | Gly | His Gly |  |
|     |     |     | 195 |     |     |     |     | 200 |     |     |     |     | 205 |         |  |

| agc | tgc | tgc | tct | gag | atg | gat | atc | tgg | gag | gcc | aac | tcc | atc | tcc gag | 720 |
|---|---|---|---|---|---|---|---|---|---|---|---|---|---|---|---|
| Ser | Cys | Cys | Ser | Glu | Met | Asp | Ile | Trp | Glu | Ala | Asn | Ser | Ile | Ser Glu |  |
|     |     | 210 |     |     |     |     | 215 |     |     |     |     | 220 |     |         |  |

| gct | ctt | acc | ccc | cac | cct | tgc | acg | act | gtc | ggc | cag | gag | atc | tgc gag | 768 |
|---|---|---|---|---|---|---|---|---|---|---|---|---|---|---|---|
| Ala | Leu | Thr | Pro | His | Pro | Cys | Thr | Thr | Val | Gly | Gln | Glu | Ile | Cys Glu |  |
|     | 225 |     |     |     |     | 230 |     |     |     |     | 235 |     |     |         |  |

| ggt | gat | ggg | tgc | ggc | gga | act | tac | tcc | gat | aac | aga | tat | ggc | ggc act | 816 |
|---|---|---|---|---|---|---|---|---|---|---|---|---|---|---|---|
| Gly | Asp | Gly | Cys | Gly | Gly | Thr | Tyr | Ser | Asp | Asn | Arg | Tyr | Gly | Gly Thr |  |
| 240 |     |     |     | 245 |     |     |     |     | 250 |     |     |     |     | 255 |  |

| tgc | gat | ccc | gat | ggc | tgc | gac | tgg | aac | cca | tac | cgc | ctg | ggc | aac acc | 864 |
|---|---|---|---|---|---|---|---|---|---|---|---|---|---|---|---|
| Cys | Asp | Pro | Asp | Gly | Cys | Asp | Trp | Asn | Pro | Tyr | Arg | Leu | Gly | Asn Thr |  |
|     |     |     | 260 |     |     |     |     | 265 |     |     |     |     | 270 |         |  |

| agc | ttc | tac | ggc | cct | ggc | tca | agc | ttt | acc | ctc | gat | acc | acc | aag aaa | 912 |
|---|---|---|---|---|---|---|---|---|---|---|---|---|---|---|---|
| Ser | Phe | Tyr | Gly | Pro | Gly | Ser | Ser | Phe | Thr | Leu | Asp | Thr | Thr | Lys Lys |  |
|     |     |     | 275 |     |     |     |     | 280 |     |     |     |     | 285 |         |  |

| ttg | acc | gtt | gtc | acc | cag | ttc | gag | acg | tcg | ggt | gcc | atc | aac | cga tac | 960 |
|---|---|---|---|---|---|---|---|---|---|---|---|---|---|---|---|
| Leu | Thr | Val | Val | Thr | Gln | Phe | Glu | Thr | Ser | Gly | Ala | Ile | Asn | Arg Tyr |  |
|     |     | 290 |     |     |     |     | 295 |     |     |     |     | 300 |     |         |  |

| tat | gtc | cag | aat | ggc | gtc | act | ttc | cag | cag | ccc | aac | gcc | gag | ctt ggt | 1008 |
|---|---|---|---|---|---|---|---|---|---|---|---|---|---|---|---|
| Tyr | Val | Gln | Asn | Gly | Val | Thr | Phe | Gln | Gln | Pro | Asn | Ala | Glu | Leu Gly |  |
|     | 305 |     |     |     |     | 310 |     |     |     |     | 315 |     |     |         |  |

| agt | tac | tct | ggc | aac | gag | ctc | aac | gat | gat | tac | tgc | aca | gct | gag gag | 1056 |
|---|---|---|---|---|---|---|---|---|---|---|---|---|---|---|---|
| Ser | Tyr | Ser | Gly | Asn | Glu | Leu | Asn | Asp | Asp | Tyr | Cys | Thr | Ala | Glu Glu |  |
| 320 |     |     |     | 325 |     |     |     |     | 330 |     |     |     |     | 335 |  |

| gca | gaa | ttc | ggc | gga | tcc | tct | ttc | tca | gac | aag | ggc | ggc | ctg | act cag | 1104 |
|---|---|---|---|---|---|---|---|---|---|---|---|---|---|---|---|
| Ala | Glu | Phe | Gly | Gly | Ser | Ser | Phe | Ser | Asp | Lys | Gly | Gly | Leu | Thr Gln |  |
|     |     |     | 340 |     |     |     |     | 345 |     |     |     |     | 350 |         |  |

| ttc | aag | aag | gct | acc | tct | ggc | ggc | atg | gtt | ctg | gtc | atg | agt | ctg tgg | 1152 |
|---|---|---|---|---|---|---|---|---|---|---|---|---|---|---|---|
| Phe | Lys | Lys | Ala | Thr | Ser | Gly | Gly | Met | Val | Leu | Val | Met | Ser | Leu Trp |  |
|     |     |     | 355 |     |     |     |     | 360 |     |     |     |     | 365 |         |  |

| gat | gat | tac | tac | gcc | aac | atg | ctg | tgg | ctg | gac | tcc | acc | tac | ccg aca | 1200 |
|---|---|---|---|---|---|---|---|---|---|---|---|---|---|---|---|
| Asp | Asp | Tyr | Tyr | Ala | Asn | Met | Leu | Trp | Leu | Asp | Ser | Thr | Tyr | Pro Thr |  |
|     |     | 370 |     |     |     |     | 375 |     |     |     |     | 380 |     |         |  |

| aac | gag | acc | tcc | tcc | aca | ccc | ggt | gcc | gtg | cgc | gga | agc | tgc | tcc acc | 1248 |
|---|---|---|---|---|---|---|---|---|---|---|---|---|---|---|---|
| Asn | Glu | Thr | Ser | Ser | Thr | Pro | Gly | Ala | Val | Arg | Gly | Ser | Cys | Ser Thr |  |
|     | 385 |     |     |     |     | 390 |     |     |     |     | 395 |     |     |         |  |

| agc | tcc | ggt | gtc | cct | gct | cag | gtc | gaa | tct | cag | tct | ccc | aac | gcc aag | 1296 |
|---|---|---|---|---|---|---|---|---|---|---|---|---|---|---|---|
| Ser | Ser | Gly | Val | Pro | Ala | Gln | Val | Glu | Ser | Gln | Ser | Pro | Asn | Ala Lys |  |
| 400 |     |     |     |     | 405 |     |     |     |     | 410 |     |     |     | 415 |  |

| gtc | acc | ttc | tcc | aac | atc | aag | ttc | gga | ccc | att | ggc | agc | acc | ggc aac | 1344 |
|---|---|---|---|---|---|---|---|---|---|---|---|---|---|---|---|
| Val | Thr | Phe | Ser | Asn | Ile | Lys | Phe | Gly | Pro | Ile | Gly | Ser | Thr | Gly Asn |  |
|     |     |     |     | 420 |     |     |     |     | 425 |     |     |     |     | 430 |  |

| cct | agc | ggc | ggc | aac | cct | ccc | ggc | gga | aac | ccg | cct | ggc | acc | acc acc | 1392 |
|---|---|---|---|---|---|---|---|---|---|---|---|---|---|---|---|
| Pro | Ser | Gly | Gly | Asn | Pro | Pro | Gly | Gly | Asn | Pro | Pro | Gly | Thr | Thr Thr |  |
|     |     |     | 435 |     |     |     |     | 440 |     |     |     |     | 445 |         |  |

| acc | cgc | cgc | cca | gcc | act | acc | act | gga | agc | tct | ccc | gga | cct | acc cag | 1440 |

```
Thr Arg Arg Pro Ala Thr Thr Gly Ser Ser Pro Gly Pro Thr Gln
        450                 455                 460 tct cac tac ggc cag tgc ggt att ggc tac agc ggc ccc acg gtc    1488
Ser His Tyr Gly Gln Cys Gly Gly Ile Gly Tyr Ser Gly Pro Thr Val
465                     470                 475 tgc gcc agc ggc aca act tgc cag gtc ctg aac cct tac tac tct cag    1536
Cys Ala Ser Gly Thr Thr Cys Gln Val Leu Asn Pro Tyr Tyr Ser Gln
480                 485                 490                 495 tgc ctgtaa                                                          1545
Cys

<210> SEQ ID NO 3
<211> LENGTH: 513
<212> TYPE: PRT
<213> ORGANISM: Trichoderma reesei

<400> SEQUENCE: 3

Met Tyr Arg Lys Leu Ala Val Ile Ser Ala Phe Leu Ala Thr Ala Arg
            -15                 -10                  -5

Ala Gln Ser Ala Cys Thr Leu Gln Ser Glu Thr His Pro Pro Leu Thr
-1   1                   5                  10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
        50                  55                  60

Asn Glu Thr Cys Ala Lys Asn Cys Cys Leu Asp Gly Ala Ala Tyr Ala
65                  70                  75

Ser Thr Tyr Gly Val Thr Thr Ser Gly Asn Ser Leu Ser Ile Gly Phe
80                  85                  90                  95

Val Thr Gln Ser Ala Gln Lys Asn Val Gly Ala Arg Leu Tyr Leu Met
            100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
            130                 135                 140

Leu Tyr Phe Val Ser Met Asp Ala Asp Gly Gly Val Ser Lys Tyr Pro
145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Gly His Gly
            195                 200                 205

Ser Cys Cys Ser Glu Met Asp Ile Trp Glu Ala Asn Ser Ile Ser Glu
        210                 215                 220

Ala Leu Thr Pro His Pro Cys Thr Thr Val Gly Gln Glu Ile Cys Glu
        225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
            260                 265                 270

Ser Phe Tyr Gly Pro Gly Ser Ser Phe Thr Leu Asp Thr Thr Lys Lys
        275                 280                 285
```

-continued

```
Leu Thr Val Val Thr Gln Phe Glu Thr Ser Gly Ala Ile Asn Arg Tyr
            290                 295                 300
Tyr Val Gln Asn Gly Val Thr Phe Gln Gln Pro Asn Ala Glu Leu Gly
305                 310                 315
Ser Tyr Ser Gly Asn Glu Leu Asn Asp Asp Tyr Cys Thr Ala Glu Glu
320                 325                 330                 335
Ala Glu Phe Gly Gly Ser Ser Phe Ser Asp Lys Gly Gly Leu Thr Gln
                340                 345                 350
Phe Lys Lys Ala Thr Ser Gly Gly Met Val Leu Val Met Ser Leu Trp
                355                 360                 365
Asp Asp Tyr Tyr Ala Asn Met Leu Trp Leu Asp Ser Thr Tyr Pro Thr
            370                 375                 380
Asn Glu Thr Ser Ser Thr Pro Gly Ala Val Arg Gly Ser Cys Ser Thr
385                 390                 395
Ser Ser Gly Val Pro Ala Gln Val Glu Ser Gln Ser Pro Asn Ala Lys
400                 405                 410                 415
Val Thr Phe Ser Asn Ile Lys Phe Gly Pro Ile Gly Ser Thr Gly Asn
                420                 425                 430
Pro Ser Gly Gly Asn Pro Pro Gly Gly Asn Pro Gly Thr Thr Thr
                435                 440                 445
Thr Arg Arg Pro Ala Thr Thr Thr Gly Ser Ser Pro Gly Pro Thr Gln
            450                 455                 460
Ser His Tyr Gly Gln Cys Gly Gly Ile Gly Tyr Ser Gly Pro Thr Val
465                 470                 475
Cys Ala Ser Gly Thr Thr Cys Gln Val Leu Asn Pro Tyr Tyr Ser Gln
480                 485                 490                 495
Cys
```

<210> SEQ ID NO 4
<211> LENGTH: 22
<212> TYPE: DNA
<213> ORGANISM: Aspergillus niger

<400> SEQUENCE: 4
gtgccccatg atacgcctcc gg       22

<210> SEQ ID NO 5
<211> LENGTH: 26
<212> TYPE: DNA
<213> ORGANISM: Aspergillus niger

<400> SEQUENCE: 5
gagtcgtatt tccaaggctc ctgacc       26

<210> SEQ ID NO 6
<211> LENGTH: 24
<212> TYPE: DNA
<213> ORGANISM: Aspergillus niger

<400> SEQUENCE: 6
ggaggccatg aagtggacca acgg       24

<210> SEQ ID NO 7
<211> LENGTH: 45
<212> TYPE: DNA
<213> ORGANISM: Aspergillus niger

<400> SEQUENCE: 7
caccgtgaaa gccatgctct ttccttcgtg tagaagacca gacag    45

<210> SEQ ID NO 8
<211> LENGTH: 45
<212> TYPE: DNA
<213> ORGANISM: Aspergillus niger

<400> SEQUENCE: 8
ctggtcttct acacgaagga aagagcatgg ctttcacggt gtctg    45

<210> SEQ ID NO 9
<211> LENGTH: 44
<212> TYPE: DNA
<213> ORGANISM: Aspergillus niger

<400> SEQUENCE: 9
ctatatacac aactggattt accatgggcc cgcggccgca gatc    44

<210> SEQ ID NO 10
<211> LENGTH: 44
<212> TYPE: DNA
<213> ORGANISM: Aspergillus niger

<400> SEQUENCE: 10
gatctgcggc cgcgggccca tggtaaatcc agttgtgtat atag    44

<210> SEQ ID NO 11
<211> LENGTH: 22
<212> TYPE: DNA
<213> ORGANISM: Trichoderma reesei

<400> SEQUENCE: 11
gcaacatgta tcggaagttg gc    22

<210> SEQ ID NO 12
<211> LENGTH: 22
<212> TYPE: DNA
<213> ORGANISM: Trichoderma reesei

<400> SEQUENCE: 12 aattaattttt acaggcactg ag    22

<210> SEQ ID NO 13
<211> LENGTH: 31
<212> TYPE: DNA
<213> ORGANISM: Saccharomyces cerevisiae

<400> SEQUENCE: 13
ttgaattgaa aatagattga tttaaaactt c    31

<210> SEQ ID NO 14
<211> LENGTH: 25
<212> TYPE: DNA
<213> ORGANISM: Saccharomyces cerevisiae

<400> SEQUENCE: 14
ttgcatgcgt aatcatggtc atagc    25

<210> SEQ ID NO 15
<211> LENGTH: 26
<212> TYPE: DNA
<213> ORGANISM: Saccharomyces cerevisiae

<400> SEQUENCE: 15

```
ttgaattcat gggtaataac tgatat                                        26

<210> SEQ ID NO 16
<211> LENGTH: 32
<212> TYPE: DNA
<213> ORGANISM: Saccharomyces cerevisiae

<400> SEQUENCE: 16
aaatcaatct attttcaatt caattcatca tt                                 32

<210> SEQ ID NO 17
<211> LENGTH: 45
<212> TYPE: DNA
<213> ORGANISM: Aspergillus oryzae

<400> SEQUENCE: 17
ggatgctgtt gactccggaa atttaacggt ttggtcttgc atccc                   45

<210> SEQ ID NO 18
<211> LENGTH: 44
<212> TYPE: DNA
<213> ORGANISM: Aspergillus oryzae

<400> SEQUENCE: 18
ggtattgtcc tgcagacggc aatttaacgg cttctgcgaa tcgc                    44

<210> SEQ ID NO 19
<211> LENGTH: 26
<212> TYPE: DNA
<213> ORGANISM: Aspergillus oryzae

<400> SEQUENCE: 19
tctgtgaggc ctatggatct cagaac                                        26

<210> SEQ ID NO 20
<211> LENGTH: 27
<212> TYPE: DNA
<213> ORGANISM: Aspergillus oryzae

<400> SEQUENCE: 20
gatgctgcat gcacaactgc acctcag                                       27

<210> SEQ ID NO 21
<211> LENGTH: 59
<212> TYPE: DNA
<213> ORGANISM: Aspergillus oryzae

<400> SEQUENCE: 21
cctctagatc tcgagctcgg tcaccggtgg cctccgcggc cgctggatcc ccagttgtg    59

<210> SEQ ID NO 22
<211> LENGTH: 33
<212> TYPE: DNA
<213> ORGANISM: Aspergillus oryzae

<400> SEQUENCE: 22
gcaagcgcgc gcaatacatg gtgttttgat cat                                33

<210> SEQ ID NO 23
<211> LENGTH: 30
<212> TYPE: DNA
<213> ORGANISM: Aspergillus oryzae
```

```
<400> SEQUENCE: 23 atcggttttta tgtcttccaa gtcgcaattg                                    30

<210> SEQ ID NO 24
<211> LENGTH: 33
<212> TYPE: DNA
<213> ORGANISM: Aspergillus oryzae

<400> SEQUENCE: 24
cttggaagac ataaaaccga tggaggggta gcg                                 33

<210> SEQ ID NO 25
<211> LENGTH: 9
<212> TYPE: DNA
<213> ORGANISM: Aspergillus oryzae

<400> SEQUENCE: 25 ggttttatg                                                            9

<210> SEQ ID NO 26
<211> LENGTH: 9
<212> TYPE: DNA
<213> ORGANISM: Aspergillus oryzae

<400> SEQUENCE: 26 gccaacatg                                                            9

<210> SEQ ID NO 27
<211> LENGTH: 33
<212> TYPE: DNA
<213> ORGANISM: Aspergillus oryzae

<400> SEQUENCE: 27
gcaagcgcgc gcaatacatg gtgttttgat cat                                 33

<210> SEQ ID NO 28
<211> LENGTH: 67
<212> TYPE: DNA
<213> ORGANISM: Aspergillus oryzae

<400> SEQUENCE: 28
gcctctagat ctcccgggcg ccggcacatg taccaggtct taagctcgag ctcggtcacc    60
ggtggcc                                                              67

<210> SEQ ID NO 29
<211> LENGTH: 33
<212> TYPE: DNA
<213> ORGANISM: Humicola insolens

<400> SEQUENCE: 29
cgcggatcca ccatgcgtac cgccaagttc gcc                                 33

<210> SEQ ID NO 30
<211> LENGTH: 30
<212> TYPE: DNA
<213> ORGANISM: Humicola insolens

<400> SEQUENCE: 30 gccccggggtt acaggcactg agagtaccag                                    30
```

METHODS FOR TRANSFORMING AND EXPRESSION SCREENING OF FILAMENTOUS FUNGAL CELLS WITH A DNA LIBRARY

CROSS-REFERENCE TO RELATED APPLICATION

This application claims the benefit of U.S. Provisional Application No. 60/575,600, filed May 27, 2004, which application is incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to methods for expression screening of filamentous fungal cells transformed with a DNA library.

2. Description of the Related Art

Commercial production of proteins frequently relies on use of recombinant host cells for expression. Prior to commercial production, research and development aimed at selecting and/or improving proteins of interest also involves use of such recombinant host cells. Screening projects, such as screening protein variants encoded by mutants of a specific gene, or screening libraries of genes from a genomic or cDNA library, are often restricted to hosts outside filamentous fungi. The most frequently utilized hosts are yeasts and bacteria, which are well-suited for high-throughput methods required for screening. Typically, thousands to hundreds of thousands of polynucleotide fragments are transformed into hosts, these transformants are cultured in a medium, and the cultures are screened for identification of proteins of interest. Often the goal is to identify or engineer a protein with improved properties, e.g., altered temperature-dependent activity profile, thermostability, pH activity, pH stability, substrate specificity, product specificity, and chemical stability.

There are, however, many limitations associated with expression screening using bacterial and yeast hosts; in some cases, the recombinant protein is in an inactive conformation, while in other cases the protein is unstable, or simply not synthesized in the first place. A protein of interest derived from a mammalian source is often poorly expressed in these hosts because either the protein expressed is in an inactive conformation or the protein is not expressed at all. In general, proteins derived from eukaryotes are expressed poorly in prokaryotic systems. Secondary modifications of recombinant proteins in these organisms may be very different from modifications that occur in the native host. Proteins from eukaryotes expressed in bacteria are unlikely to be correctly glycosylated, as these modifications occur in the secretory pathway, which is not present in bacteria. The most commonly used yeast strain, *Saccharomyces cerevisiae*, often hyper-glycosylates proteins, which can lead to expression of inactive proteins compared to their native states.

Another complication of using a bacterial or yeast host for enzyme screening is that the screening host is usually different from the final production host that is used industrially. There are important time and technical considerations involved in switching hosts. Even if an enzyme is successfully expressed in both types of hosts, expression constructs must be re-engineered when shifting from screening to production. More importantly, proteins that have been subjected to directed evolution, i.e., random mutagenesis, recombination, and selection of improved properties over generations of screening, may evolve to acquire improved properties that are specific to the screening host, perhaps by affecting folding and/or modification in a host-specific manner.

Another consideration for enzyme screening is the yield of expressed protein. While bacteria often produce very high yields of recombinant prokaryotic protein, poor yields of soluble, active protein are frequently observed when eukaryotic proteins are expressed in prokaryotes. Yeast hosts are often unable to support high levels of recombinant protein expression. Assays for biological activity during screening must be sufficiently sensitive to detect very low levels of protein. Often, detection is not possible, especially when the protein of interest has a poor specific activity. Furthermore, it is often advantageous to express proteins at a sufficient level such that detection of their activity can easily be distinguished over low levels of competing endogenous biological activity in the host strain. These concerns explain the frequent choice of a filamentous fungal host for production of eukaryotic genes, as these organisms often support high levels of protein expression. Screening is often crippled by poor yields obtained in commonly used yeast and bacteria hosts.

While filamentous fungal hosts have obvious advantages over bacterial and yeast hosts, high-throughput expression screening of filamentous fungal cultures is complicated by features of fungal morphology. For example, hyphae tend to clog pipet tips of liquid handlers, mycelial mats make it difficult to access liquid phase of cultures, and automated picking and inoculation of single filamentous fungal transformants on agar plates is not as routine as for yeasts and bacteria colonies.

Generating transformants that express a single type polypeptide is desirable when screening for novel or improved properties. Expression of a single type of polypeptide allows detection of small changes in protein performance. In contrast, working with transformed organisms that co-express more than a single type of polypeptide is technically challenging, because the screen sensitivity must be sufficient to detect a unique property of a protein that is present in a background of proteins having distinct properties. It is generally an advantage to have an expression screening host where a single type of polynucleotide fragment is introduced into each single transformant.

The process of introducing a single type of polynucleotide into a bacterial or yeast host is well known in the art. In bacteria, plasmid replicons can be used to prevent two different plasmids from coexisting in the same bacterial cell (Davidson, 1984 Gene 28: 1-15). Often, a library to be screened comprises a heterogenous population of plasmids, each including the same replicon, which is transformed into a pool of bacterial or yeast competent cells. When plasmids containing foreign genes are introduced into bacterial cells, the consequent outgrowth of the population leads to segregation of plasmids such that each cell contains only a single type of plasmid. Over the course of a few generations of bacterial growth, the minority plasmid is completely eliminated and the descendants of the original cell contain one plasmid or the other, but not both. Plasmids carrying the same replicon thus are said to belong to the same incompatibility group (Datta, 1979, in *Plasmids of Medical, Environmental, and Commercial Importance*, Timmis and Puhler, eds. Elsevier, Amsterdam).

Transformation of bacteria with a library of a heterogenous population of plasmids thus results in restriction of a single type of plasmid per transformant. On the other hand, the process of introducing a single type of polynucleotide into a filamentous fungal expression host is not as simple when transforming with a DNA library, which comprises a heterogeneous population of plasmids. When filamentous fungal strains are genetically engineered by introduction of foreign polynucleotide sequences, two different types of methods are routinely used. One method allows for integration of DNA into the fungal host chromosome. Frequently, more than a single polynucleotide fragment is introduced (Alesenko, 1994, *Curr Genet* 26:352-358). Another means of introducing the foreign DNA is to use an autonomously replicating plasmid. With both types of transformation, it is possible for a single host to contain more than one distinct polynucleotide fragment from the library that was used in transformation. The filamentous fungus is often multicellular and frequently multinucleate. It is common in the art to utilize spore purification in order to attempt to segregate unique polynucleotide fragments that were introduced into individual hosts. This process is time-consuming and difficult to automate, as colony picking robots do not easily pick filamentous fungal colonies for inoculation into liquid culture or for re-arraying for solid phase culture.

Restriction of genetic material so that individual transformants contain only a single type of polynucleotide fragment would be an advantage in the art of screening a filamentous fungal expression library. Specifically, it would be advantageous to have available a high-throughput method for transformation of filamentous fungi, where expression is relatively high, and where recovering genes from those transformants identified by a screen is fast and easy.

In addition to the advantages conferred in expressing individual DNA fragments from a DNA library in individual filamentous fungal transformants, it is also advantageous to have a facile method for recovering the foreign polynucleotide from transformants identified in the screen. Typically, a DNA rescue procedure is employed for plasmid transformants (such as AMA1 and ANS1 containing vectors) whereby a DNA preparation is made from the transformant, and this preparation is then used to transform *E. coli* in order to prepare suitable amounts of the plasmid for sequence analysis. For recovery of transformed DNA in filamentous fungal transformants where DNA has been integrated into the host chromosome, amplification of the foreign gene using PCR and genomic DNA prepared from the transformant is a commonly used method. Alternatively, one can prepare RNA from the transformant under conditions where the recombinant gene is expressed, and amplify the foreign polynucleotide from nucleic acid derived from the RNA. The common feature of all these nucleotide recovery methods is that they are time-consuming steps. It would be advantageous to have a quick and easy step for recovering the nucleotide material from an isolated filamentous fungal transformant that was derived from library expression screening.

WO 00/24883 discloses a general method for constructing and screening a cDNA library using an AMA plasmid in filamentous fungal cells.

An example of high throughput screening of filamentous fungal cultures is described by Lamsa and Bloebaum, 1990, *J. Ind. Microbiol.* 5: 229-238.

It is an object of the present invention to provide methods for single-well transformation and expression screening.

SUMMARY OF THE INVENTION

The present invention relates to methods for expression screening of filamentous fungal transformants, comprising:
(a) isolating single colony transformants of a DNA library introduced into *E. coli*;
(b) preparing DNA from each of the single colony *E. coli* transformants;
(c) introducing a sample of each of the DNA preparations of step (b) into separate suspensions of protoplasts of a filamentous fungus to obtain transformants thereof, wherein each transformant contains one or more copies of an individual polynucleotide from the DNA library;
(d) growing the individual filamentous fungal transformants of step (c) on selective growth medium, thereby permitting growth of the filamentous fungal transformants, while suppressing growth of untransformed filamentous fungi; and
(e) measuring activity or a property of each polypeptide encoded by the individual polynucleotides.

In a preferred aspect, recovery of the polynucleotide encoding a polypeptide of interest in the transformants that are identified in the screen can be performed by collecting the corresponding DNA prepared in step (b) that has been archived and stored.

In another preferred aspect, the methods of the present invention are performed manually. In a more preferred aspect, the methods of the present invention are automated for high-throughput expression screening.

In another preferred aspect, the DNA library is a library of mutants of a gene, wherein the mutated genes encode polypeptide variants.

In another preferred aspect, the methods further comprises isolating from one or more of the individual *E. coli* transformants a polynucleotide originating from the DNA library, wherein the polynucleotide encodes a polypeptide of interest.

In another preferred aspect, the methods further comprises isolating from one or more of the individual filamentous fungal transformants a polynucleotide originating from the DNA library, wherein the polynucleotide encodes a polypeptide of interest.

The present invention also relates to isolated polynucleotides encoding polypeptides of interest obtained by such methods, to nucleic acid constructs, expression vectors, and recombinant host cells comprising the isolated polynucleotides, and to methods of producing the polypeptides encoded by the isolated polynucleotides.

DEFINITIONS

Figure 1:
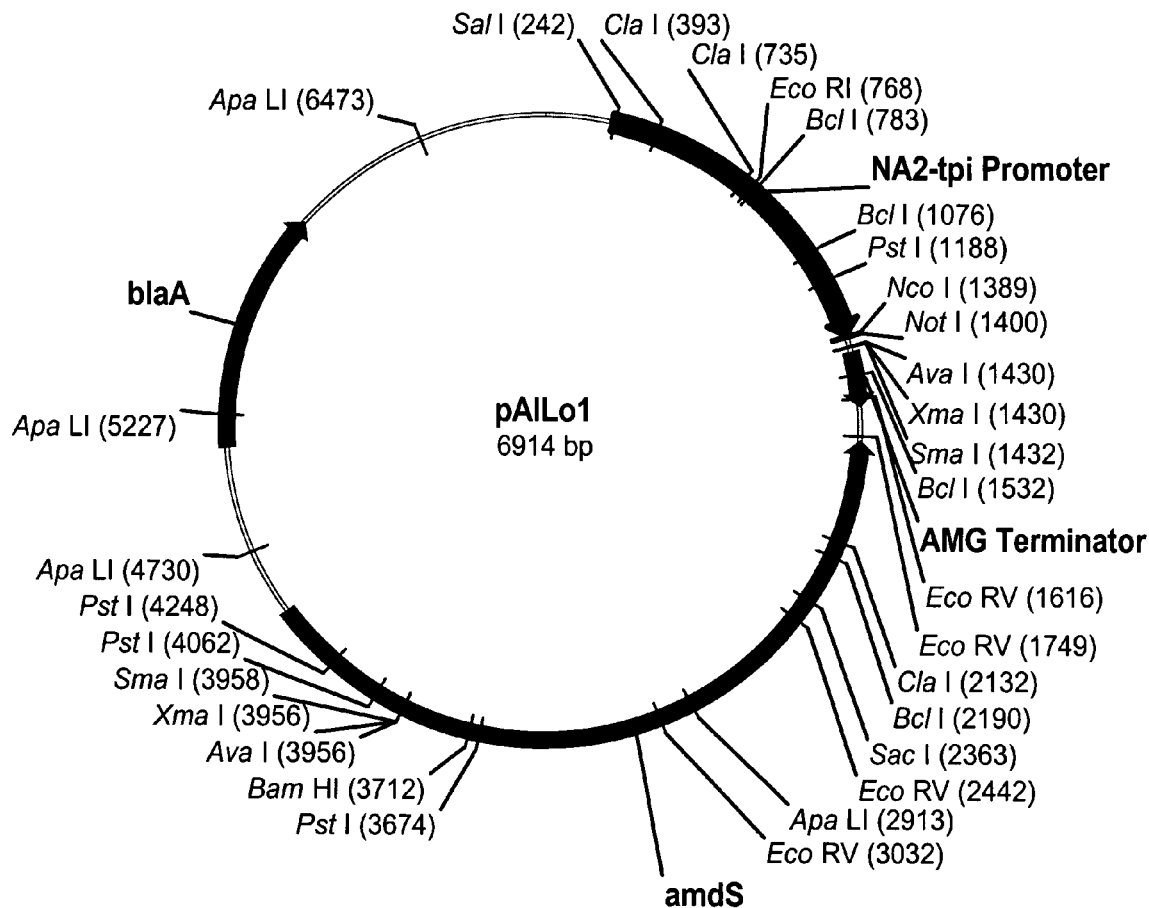
FIG. 1 shows a restriction map of pAlLo1.

Expression screening: The term "expression screening" is defined as the expression of polypeptides encoded by DNA fragments of a DNA library in a selected host and assaying properties of the expressed polypeptides. The method entails transformation of library fragments in a suitable expression vector into a selected expression host, so that open reading frames of the DNA library will either be transcribed from their own promoter, or from a promoter in the cloning vector.

Mutant: The term "mutant" is defined herein as a mutated polynucleotide encoding a polypeptide comprising one or more alterations, such as substitutions, insertions, deletions, and/or truncations of one or more specific amino acid residues at one or more specific positions compared to the parent polypeptide.

Variant: The term "variant" is defined herein as a polypeptide comprising one or more alterations, such as substitutions, insertions, deletions, fusions, and/or truncations of one or more specific amino acid residues at one or more specific positions in the polypeptide.

Wild-type polypeptide: The term "wild-type polypeptide" denotes a polypeptide expressed by a naturally occurring microorganism.

Parent polypeptide: The term "parent polypeptide" as used herein means a polypeptide to which one or more modifications, e.g., substitutions, insertions, deletions, and/or truncations, are made to produce polypeptide variants. This term also refers to the polypeptide with which a variant is compared and aligned. The parent may be a naturally occurring (wild-type) polypeptide, or the parent protein may be a variant of a naturally occurring polypeptide that has been modified or altered in the amino acid sequence, prepared by any suitable means. A parent may also be an allelic variant of a polypeptide that is encoded by any of two or more alternative forms of a gene occupying the same chromosomal locus.

Modification: The term "modification" means herein any chemical modification of a polypeptide as well as genetic manipulation of DNA. The modification can be substitutions, deletions and/or insertions of one or more amino acids as well as replacements of one or more amino acid side chains.

Selective medium: The term "selective medium" is defined herein as a liquid or solid nutrient-containing mixture that allows growth of transformed microorganisms, but does not allow growth of untransformed cells. Selection can be obtained by inclusion of a substance in the medium that is toxic to the untransformed organism, such that when an expression vector containing a selective marker is present in a transformed microorganism, expression of the marker detoxifies the toxin or otherwise provides resistance to it. Selection can also be obtained by utilizing a microorganism that is unable to grow in the absence of a supplemental nutrient. For example, an auxotrophic mutant can be subjected to transformation and selection can be provided by screening in the absence of a needed metabolite that can only be synthesized by strains containing an expression vector sequence which provides a polynucleotide sequence required for synthesis of the metabolite.

Shuffling: The term "shuffling" means recombination of at least one nucleotide sequence between two or more homologous polynucleotides resulting in recombined nucleotide sequences (i.e., nucleotide sequences having been subjected to a shuffling cycle) having a number of nucleotides exchanged, in comparison to the starting nucleotide sequences of the polynucleotides.

DNA library: The term "DNA library" is defined herein as a collection of recombinant expression vectors or plasmids containing inserts (DNA fragments) from a single genome, two or more genomes, mutated DNA, shuffled DNA, and the like. The vectors may be linear or closed circular plasmids. The origin of the insert DNA can be genomic, cDNA, semi-synthetic, synthetic, or any combinations thereof.

Randomized library or variant library: The term "randomized library", or "variant library," is defined herein as a library of mutated polynucleotides. Diversity in the variant library can be generated via mutagenesis of the genes encoding the variants at the DNA triplet level, such that individual codons are variegated, e.g., by using primers of partially randomized sequence in a PCR reaction. Several techniques have been described, by which one can create a diverse combinatorial library by variegating several nucleotide positions in a gene and recombining them, for instance, where these positions are too far apart to be covered by a single (spiked or doped) oligonucleotide primer. "Spiked mutagenesis" is a form of site-directed mutagenesis, in which the primers used have been synthesized using mixtures of oligonucleotides at one or more positions. These techniques include the use of in vivo recombination of the individually diversified gene segments as described in WO 97/07205. They also include the use of DNA shuffling techniques to create a library of full length genes, wherein several gene segments are combined, and wherein each segment may be diversified, e.g., by spiked mutagenesis (Stemmer, 1994, *Nature* 370: 389-391; U.S. Pat. No. 5,811,238; U.S. Pat. No. 5,605,793; and U.S. Pat. No. 5,830,721). One can use a gene encoding a protein "backbone" (wild-type parent polypeptide) as a template polynucleotide, and combine this with one or more single or double-stranded oligonucleotides as described in WO 98/41623 and WO 98/41622. The single-stranded oligonucleotides can be partially randomized during synthesis. The double-stranded oligonucleotides can be PCR products incorporating diversity in a specific region. In both cases, one can dilute the diversity with corresponding segments encoding the sequence of the backbone protein in order to limit the average number of changes that are introduced.

Recombination: The term "recombination" is defined herein as the process wherein nucleic acids associate with each other in regions of homology, leading to interstrand DNA exchange between those sequences. For purposes of the present invention, homologous recombination is determined according to the procedures summarized by Paques and Haber, 1999, *Microbiology and Molecular Biology Reviews* 63: 349-404. "Homologous recombination" is defined herein as recombination in which no changes in the nucleotide sequences occurs within the regions of homology relative to the input nucleotide sequences. For perfect homologous recombination, the regions should contain a sufficient number of nucleotides, such as 15 to 10,000 base pairs, preferably 100 to 10,000 base pairs, more preferably 400 to 10,000 base pairs, and most preferably 800 to 10,000 base pairs, which are highly homologous with the corresponding nucleotide sequence to enhance the probability of homologous recombination. The recombination may also occur by non-homologous recombination. "Non-homologous recombination" is defined herein as recombination where any mode of DNA repair incorporating strand exchange results in a nucleotide sequence different from any of the recombining sequences.

Improved property: The term "improved property" is defined herein as a characteristic associated with a variant polypeptide which is improved compared to the parent polypeptide, e.g., enzyme. Such improved properties include, but are not limited to, altered temperature-dependent activity profile, thermostability, pH activity, pH stability, substrate specificity, product specificity, and chemical stability.

Improved thermal activity: The term "improved thermal activity" is defined herein as a variant polypeptide having biological activity, e.g., enzyme, displaying an alteration of the temperature-dependent activity profile of the variant at a specific temperature relative to the temperature-dependent activity profile of the parent polypeptide. For example, with an enzyme, the thermal activity value provides a measure of an enzyme's efficiency in performing catalysis of a reaction, e.g., hydrolysis, over a range of temperatures. An enzyme has a specific temperature range wherein the protein is stable and retains its enzymatic activity, but becomes less stable and thus less active with increasing temperature. Furthermore, the initial rate of a reaction catalyzed by an enzyme can be accelerated by an increase in temperature which is measured by determining thermal activity of a variant. A more thermoactive variant will lead to an increase in the rate of reaction decreasing the time required and/or decreasing the enzyme concentration required. Alternatively, a variant with a reduced thermal activity will catalyze a reaction at a temperature lower than the temperature optimum of the parent enzyme defined by the temperature-dependent activity profile of the parent.

Improved thermostability: The term "improved thermostability" is defined herein as a variant polypeptide having biological activity displaying retention of biological activity after a period of incubation at elevated temperature relative to the parent polypeptide. Such a variant may or may not display an altered thermal activity profile relative to the parent, e.g., it may have an improved ability to refold following incubation at elevated temperature relative to the parent.

Improved product specificity: The term "improved product specificity" is defined herein as a variant polypeptide having biological activity displaying an altered product profile relative to the parent in which the altered product profile improves the performance of the variant in a given application relative to the parent. The term "product profile" is defined herein as the chemical composition of the reaction products produced by the biological activity, e.g., enzyme activity.

Improved chemical stability: The term "improved chemical stability" is defined herein as a variant polypeptide displaying retention of biological activity after a period of incubation in the presence of a chemical or chemicals, either naturally occurring or synthetic, which reduce the biological activity of the parent polypeptide. Improved chemical stability may also result in variants better able to perform their biological activity, e.g., catalyze an enzymatic reaction, in the presence of such chemicals.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Polypeptide Fragment: The term "polypeptide fragment" is defined herein as a polypeptide having one or more amino acids deleted from the amino and/or carboxyl terminus of a polypeptide, wherein the fragment retains biological activity.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Subsequence: The term "subsequence" is defined herein as a nucleotide sequence having one or more nucleotides deleted from the 5' and/or 3' end of an isolated polynucleotide, wherein the subsequence encodes a polypeptide fragment having biological activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of interest. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TM, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector/plasmid: The term "expression vector" or "expression plasmid" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide encoding a polypeptide of interest.

Transformant: A "transformant" is used herein to refer to a microorganism that has been genetically modified by introduction of a polynucleotide fragment. The process by which the DNA is introduced, e.g., transformation, transfection, transduction, and the like, to produce a transformant can entail DNA derived from a different organism than the host, or can entail use of DNA that is derived from the same species.

DETAILED DESCRIPTION OF THE INVENTION

The present invention relates to methods for expression screening of filamentous fungal transformants, comprising: (a) isolating single colony transformants of a DNA library introduced into *E. coli*; (b) preparing DNA from each of the single colony *E. coli* transformants; (c) introducing a sample of each of the DNA preparations of step (b) into separate suspensions of protoplasts of a filamentous fungus to obtain transformants thereof, wherein each transformant contains one or more copies of an individual polynucleotide from the DNA library; (d) growing the individual filamentous fungal transformants of step (c) on selective growth medium, thereby permitting growth of the filamentous fungal transformants, while suppressing growth of untransformed filamentous fungi; and (e) measuring activity or a property of each polypeptide encoded by the individual polynucleotides.

The present invention allows for recovery of the DNA material in those transformants identified in the screen that express polypeptides with desired activities or properties. Alternatively, instead of trying to recover, amplify, or rescue the foreign gene from an *E. coli* or filamentous fungal transformant, one can also utilize archived DNA samples from step (b). One simply determines which of the individual DNA preparations was used to generate a specific transformant, and retrieves an aliquot of stored archived DNA that was used in the original transformation.

The steps in the methods of the present invention may be performed manually or by automation. For high-throughput expression screening, it is preferable that the methods of the present invention are automated. In a preferred aspect, one or more steps are automated. In a more preferred aspect, each step is automated.

Use of robots and other automated devices in the laboratory is common in the art, and are often used to manipulate cultures of bacteria and yeasts (Reichman et al., 1996, *Lab. Robot. and Automat* 8: 267-276; Olsen et al., 2000, *Curr. Opin. Biotech.* 11: 331-337; Zhao and Arnold, 1997, *Curr. Opin. Struct. Biol.* 7: 480-485; Berg et al., 2000, *J. of Biomolecular Screening*, 5: 71-76; Evans et al., 2002, *J. of Biomolecular Screening*, 7: 359-366; Cherry et al., 1999, *Nature Biotechnol.* 17: 379-384). Use of robotics to manipulate living filamentous fungi is, however, rare (Arhoun, et al, 1999, *Lab Robot and Automat* 11: 121-126). The present invention preferably utilizes multiwell plates (also called microtiter plates) for manipulation of microorganisms, DNA, polypeptides, and other molecules. However, commercial systems usually can work with any well-plate configuration that has the same footprint as a standard 96-well plate; 12.8 cm×8.6 cm. Most systems allow the user to configure a custom plate within these dimensions. Nearly any style of standard plastic or glass tube that can be mounted in some way in a rack on the particular robot can be used. In many cases, the tube rack is a standard microtiter plate footprint. In fact, some systems have their own racks to fit a wide array of test tubes. Commonly used robots include three basic types. One type of robot is used to pick microorganisms from culture on solid media, and transfer these specific organisms to either liquid growth media, or to solid culture media. Another type of robot, the liquid handling robot, moves liquids from place to place, e.g., from a test tube to a multiwell plate. A third type of robot moves consumable items such as reagent reservoirs, multiwell plates, or pipet tips. Other automation devices may fit into more than one of these classes, or may fall outside these general classifications.

DNA Libraries

Vectors/Plasmids for DNA Libraries

DNA libraries are a collection of recombinant vectors containing inserts (DNA fragments) from a single genome, two or more genomes, mutated DNA, shuffled DNA, and the like. The origin of the insert DNA can be genomic, cDNA, semi-synthetic, synthetic, or any combinations thereof.

Each insert comprises a nucleotide sequence encoding a polypeptide of interest having biological activity or a fragment thereof which retains biological activity.

The polypeptide may be any polypeptide having a biological activity of interest. The polypeptide may be native or heterologous to the filamentous fungal cell employed in the screen. Moreover, the polypeptide may be a variant of a parent polypeptide. The term "polypeptide" is not meant herein to refer to a specific length of the encoded product and, therefore, encompasses peptides, oligopeptides, and proteins. The term "polypeptide" also encompasses naturally occurring allelic or engineered variants of a polypeptide.

In a preferred aspect, the polypeptide is an antibody, antigen, antimicrobial peptide, enzyme, growth factor, hormone, immunodilator, neurotransmitter, receptor, reporter protein, structural protein, transcription factor, and transporter.

In a more preferred aspect, the polypeptide is an oxidoreductase, transferase, hydrolase, lyase, isomerase, or ligase. In a most preferred aspect, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is a collagen or a gelatin.

The vectors used may be any plasmid (or vector) that can be subjected to recombinant DNA procedures to ligate or introduce the inserts. The plasmid should be a shuttle plasmid which can be maintained and replicated in *E. coli* and which can then be used to transform a filamentous fungal host.

In a preferred aspect, the plasmids of a library preferably comprise an element(s) that permits autonomous replication of the plasmid in the cell independent of the genome or integration of the vector into the host cell's genome.

For autonomous replication, the plasmid may further comprise an origin of replication enabling the plasmid to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or plasmid to replicate in vivo.

The plasmid replicator may be any plasmid replicator mediating autonomous replication which functions in a cell. Examples of bacterial origins of replication are the origins of replication of plasmids pBR322, pUC19, pACYC177, and pACYC184 permitting replication in *E. coli*. Examples of a plasmid replicator useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

For integration into the host cell genome, the plasmid may rely on the polynucleotide's sequence encoding the polypeptide or any other element of the plasmid for integration into the genome by homologous or nonhomologous recombination. Alternatively, the plasmid may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the plasmid may be integrated into the genome of the host cell by non-homologous recombination. Because multiple copies of a gene can be integrated into the chromosome, this can facilitate high level expression by boosting gene copy number. An advantage of the present invention is that upon integration of a foreign insert into a filamentous host, one can be assured that only a single type of insert will be introduced.

In some cases, the linearization of a plasmid can improve the frequency of integration into the fungal chromosome. The linearizing of the plasmid(s) can be directed toward any site within the plasmid. The plasmid(s) may be linearized by any suitable methods known in the art, for example, digestion with one or more restriction enzymes.

To facilitate the screening process, the plasmid is preferably an expression vector in which the insert is operably linked to one or more control sequences which direct the expression of the coding sequence of the insert in a suitable filamentous fungal host cell under conditions compatible with the control sequences. Control sequences for bacteria and fungi are described herein.

The plasmid preferably contains one or more selectable markers described herein which permit easy selection of transformed cells.

In general, the expression vector is derived from a plasmid, a cosmid, or a bacteriophage, or may contain elements of any or all of these. For purposes of the present invention, the terms "plasmid" and "vector" are used interchangeably.

Sources of DNA Fragments for Libraries

The DNA fragments (or inserts) contained within the library plasmids may be prepared by a number of methods. For instance, the DNA fragments may be prepared by PCR amplification using specific primers, for example, as described in U.S. Pat. No. 4,683,202 or Saiki et al., 1988, *Science* 239: 487-491. Library DNA fragments may alternatively be prepared synthetically by established standard methods, e.g., the phosphoamidite method described by Beaucage and Caruthers, 1981, *Tetrahedron Letters* 22: 1859-1869, or the method described by Matthes et al., (1984), *EMBO Journal* 3: 801-805.

The DNA fragments may also be of mixed synthetic and genomic, mixed synthetic and cDNA, or mixed genomic and cDNA origin prepared by ligating fragments of synthetic, genomic or cDNA origin, the fragments corresponding to various parts of the entire nucleotide sequence, in accordance with standard techniques. Futhermore the DNA fragments may be prepared by PCR amplification of nucleic acid including DNA, cDNA, and RNA, and may be isolated using standard methods known in the art. For example, cDNA probes may be obtained from the total polyadenylated mRNA isolated from cells of an organism or organisms using standard methods and reverse transcribed into total cDNA.

The DNA library may be obtained from any organism, including, but not limited to, microorganisms, plants, and mammals. For purposes of the present invention, the term "obtained from" as used herein in connection with a given source shall mean that a polynucleotide sequence is produced by the source or by a strain in which the polynucleotide sequence from the source has been inserted.

In a preferred aspect, the DNA library is obtained from a bacterium such as a gram positive bacterium.

In a more preferred aspect, the DNA library is obtained from a *Bacillus, Pseudomnas, Streptomyces*, or *E. coli* strain.

In a most preferred aspect, the DNA library is obtained from *Bacillus alkalophilus, Bacillus amyloliquefaciens, Bacillus brevis, Bacillus circulans, Bacillus coagulans,*

*Bacillus lautus, Bacillus lentus, Bacillus licheniformis, Bacillus megaterium, Bacillus stearothermophilus, Bacillus subtilis, Bacillus thuringiensis, Streptomyces lividans*, or *Streptomyces murinus*.

In another preferred aspect, the DNA library is obtained from a yeast such as a *Candida, Kluyveromyces, Pichia, Saccharomyces, Schizosaccharomyces*, or *Yarrowia* strain; or a filamentous fungus such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* strain.

In a more preferred aspect, the DNA library is obtained from *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis*.

In another more preferred aspect, the DNA library is obtained from *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammiung von Mikroorganismen und Zellkulturen GmbH (DSM), Centraalbureau Voor Schimmelcultures (CBS), and Agricultural Research Service Patent Culture Collection, Northern Regional Research Center (NRRL).

The DNA library may also be obtained from an uncultivated collection of organisms sampled from a given environmental location (Liles et al., 2003, *Appl. Environ. Microbiol.* 69: 2684-2691; Beja et al., 2000, *Science* 289: 1902-1906; Tyson et al., 2004, *Nature* 428: 37-43; Venter et al., 2004, *Science* 304: 66-74, U.S. Pat. No. 6,723,504).

In another preferred aspect, the DNA library is obtained from a nucleotide material purified directly from or amplified from an environmental sample, including a collection of uncultivated organisms, such as from a soil sample, a freshwater sample, a saltwater sample, an insect gut, an animal stomach, waste water, sludge, or sediment.

Libraries of Mutated Genes Encoding Variant Polypeptides

The methods of the present invention can also be used for expression screening of variants of a parent polypeptide. Such variants can comprise a modification of the parent polypeptide such as a substitution, insertion and/or deletion at one or more positions of the parent polypeptide or can also comprise hybrid polypeptides or protein fusions.

Mutations can be introduced by procedures known in the art, such as PCR, or error prone PCR. The PCR amplification may be combined with a mutagenesis step using a suitable physical or chemical mutagenizing agent, e.g., one which induces transitions, transversions, inversions, scrambling, substitutions, deletions, and/or insertions. In a preferred aspect of the present invention, the DNA fragment or fragments are prepared under conditions resulting in a low, medium or high random mutagenesis frequency. To obtain low mutagenesis frequency the nucleotide sequence(s) (comprising the DNA fragment(s)) may be prepared by a standard PCR amplification method (U.S. Pat. No. 4,683,202 or Saiki et al., 1988, *Science* 239: 487-491). A medium or high mutagenesis frequency may be obtained by performing the PCR amplification under conditions which reduce the fidelity of replication by a thermostable polymerase and increase the misincorporation of nucleotides, for instance as described by Deshler, 1992, *GATA* 9: 103-106; Leung et al., 1989, *BioTechniques* 1: 11-15.

Other methods for producing libraries of mutated genes are known in the art, such as oligonucleotide-directed mutagenesis, assembly PCR, in vivo mutagenesis, site-specific mutagenesis, region-directed mutagenesis, and oligonucleotide cassette mutagenesis (Reidhaar-Olson and Sauer, 1988, *Science* 241: 53-57; Bowie and Sauer, 1989, *Proc. Natl. Acad. Sci. USA* 86: 2152-2156; WO 95/17413; WO 95/22625; Lowman et al., 1991, *Biochem.* 30: 10832-10837; U.S. Pat. No. 5,223,409; WO 92/06204; Derbyshire et al., 1986, *Gene* 46: 145; Ner et al., 1988, *DNA* 7: 127).

Mutations can be also be introduced and recombined by procedures such as in vivo and in vitro shuffling. The library of DNA fragments can be randomly combined (or "shuffled") with homologous regions in a linearized plasmid(s) by in vivo recombination (Cherry et al., *Nat Biotechnol.* 17: 379-384) or by in vitro shuffling methods by random fragmentation and polymerase chain reaction (PCR) reassembly (Stemmer et al., 1994, *Nature* 370:389-91; U.S. Patent Application No. 20030054390). A large number of mutants or homologous genes can be combined in one transformation to efficiently create gene chimeras from the homologous genes. The shuffling of these genes, encoding improved variants or wild-type genes, results in chimeras that can be expressed and followed by screening to identify those chimeras with the optimal combination of beneficial mutations. The process increases multi-fold the number of further improved variants that can be obtained compared to a process that uses only random mutagenesis (for a review, see Kuchner and Arnold, 1997, *TIBTech* 15: 523-530).

Random mutagenesis introduces mutations into a target nucleotide sequence, creating deleterious mutations much more frequently than beneficial ones. In iterative rounds of such mutagenesis, deleterious mutations accumulate more rapidly than beneficial ones, effectively masking the identification of beneficial mutations during screening. The random recombination between two or more homologous nucleotide sequences that contain multiple single nucleotide changes in their nucleotide sequences potentially allows all those nucleotide changes contained in one mutant to be separated from one another and to be randomly combined instead with any mutations present on other mutants. This shuffling of mutations provides a means by which mutations from different parent sequences can be combined with each other randomly to increase the probability of combining nucleotide changes in a single nucleotide sequence. It is preferred that at least one shuffling cycle is a backcrossing cycle with the initially used DNA fragment or fragments, which may be the wild-type DNA fragment. This eliminates non-essential mutations.

Non-essential mutations may also be eliminated by using wild-type DNA fragments as the initially used input DNA material.

Efficient recombination of multiple overlapping fragments using the in vivo recombination method is a means to generate chimeras from mutants or homologous genes. An overlap as small as 15 bp is sufficient for recombination, and may be utilized for very easy domain shuffling of even distantly related genes. In domain shuffling, larger blocks of non-homologous DNA are randomly assorted by means of stretches of homology at their termini. Employing overlapping fragments is a useful method for domain shuffling by creating small overlaps between DNA fragments from different domains and screening for the best combination.

Mutagenesis/shuffling methods can be combined with the high-throughput, automated screening methods of the present invention to detect activity of cloned, mutagenized polypeptides expressed by host cells. Mutagenized DNA molecules that encode active variant polypeptides can be recovered from archived *E. coli* transformants, or alternatively, recovered from fungal cells and rapidly sequenced using standard methods in the art. These methods allow the rapid determination of the importance of individual amino acid residues in a polypeptide of interest, and can be applied to polypeptides of unknown structure.

*E. coli* Hosts

In the methods of the present invention, any *E. coli* strain may be utilized to isolate single colony transformants of a DNA library introduced into the *E. coli* strain. Examples of *E. coli* strains useful in the practice of the present invention include, but are not limited to, DH5α™ (Invitrogen, Carlsbad, Calif.) [F− 80dlacZΔM15 Δ(lacZYA-argF) U169 recA1 endA1 hscR17($r_k^-$, $m_k^+$) phoA supE44 λ− thi-1 gyrA96 relA1]; One Shot® INValphaF' (Invitrogen, Carlsbad, Calif.) [F' endA1 recA1 hscR17 (rk−, mk+) supE44 thi-1 gyrA96 relA1 φ80lacZ.15.(lacZYA-argF)U169 λ−]; Top10 (InVitrogen, Carlsbad, Calif.) F− mcrA Δ(mrr-hscRMS-mcrBC) φ80lacZΔM15 ΔlacX74 recA1 araΔ139 Δ(ara-leu)7697 galU galK rpsL ($Str^R$) endA1 nupG.

The introduction of a DNA library into *E. coli* may be achieved through the use of chemically competent or electroporation competent *E. coli* cells. For example, introduction of a DNA library can be accomplished with SURE® Electroporation-Competent Cells (Stratagene, La Jolla, Calif., U.S. Pat. Nos. 6,338,965, 6,040,184, 6,017,748, and 5,552,314 and equivalent foreign patents), XL1-Blue Electroporation-Competent Cells (Stratagene, La Jolla, Calif., U.S. Pat. Nos. 6,338,965 and 6,040,184), XL10-Gold® Ultracompetent Cells (Stratagene, La Jolla, Calif., U.S. Pat. Nos. 5,512, 468 and 5,707,841), and SURE® Competent Cells (Stratagene, La Jolla, Calif., U.S. Pat. Nos. 6,017,748, 5,707,841, 5,552,314, and 5,512,468; U.S. Pat. Nos. 6,017,748, and 5,552,314; and U.S. Pat. Nos. 6,338,965, 6,040,184, 6,017, 748, and 5,552,314).

The isolation of single colony *E. coli* transformants of the DNA library can be accomplished manually or using a colony-picking device. Any commercially available device may be used. Such devices include, but are not limited to, Genetix QPix (Genetix Limited, Hampshire, UK); VersArray Colony Picker and Arrayer System (BioRad, Hercules, Calif., USA).

The single colony *E. coli* transformants of step (a) can be transferred into individual wells of a multiwell plate, which can be accomplished manually or using a colony-picking device, as described above.

Isolation of DNA from *E. coli* Transformants

In the methods of the present invention, the step of preparing DNA from each of the single colony *E. coli* transformants can be performed in any format known in the art. Preparation of the DNA is preferably performed in the individual wells of a multiwell plate. The preparation of the DNA can be accomplished using any procedure known in the art. See, for example, Sambrook, et al., 1989, *Molecular Cloning: a Laboratory Manual* Cold Spring Harbor Laboratory Press, 2$^{nd}$ Ed., pp 1.21-1.49, for methods for boiling, SDS, and alkali lysis, and purification by methods such as cesium chloride gradient. DNA can be isolated using a 96-well Miniprep Kit protocol of Advanced Genetic Technologies Corporation (Gaithersburg, Md.) as modified by Utterback et al. (1995, *Genome Sci. Technol.* 1:1-8). In addition, rolling-circle amplification may be used to prepare DNA from single colony *E. coli* transformants (Nelson et al., 2002, *Biotechniques*, June, Suppl: 44-47).

In a preferred aspect, the step of preparing the DNA is automated. For example, plasmid DNA from *E. coli* strains can be prepared using a robotic device, e.g., a BioRobot 9600 (QIAGEN Inc., Valencia, Calif.). Plasmid DNA can also be isolated from the cultures using a QIAGEN Qiabot Miniprep Station (QIAGEN Inc., Valencia, Calif.) following the manufacturer's instructions. Another device is the AutoGenprep 960 instrument (AutoGen, Inc., Holliston, Mass.) that is a fully automated high-throughput instrument for DNA extraction in a 96-well format.

In another preferred aspect, a fraction or aliquot of the total DNA prepared from single colony *E. coli* transformants is used for transformation of filamentous fungi, and the remaining fraction is stored. This archive of the DNA library used for transformation allows easy recovery of nucleotide material in those transformants identified for follow-up by the expression screen.

Transformation of Filamentous Fungal Host

In the methods of the present invention, each of the DNA preparations of step (b) are introduced into separate suspensions of protoplasts of a filamentous fungus cell to obtain transformants thereof, using any format known in the art. Each transformant will contain one or more copies of an individual polynucleotide from the DNA library. Transformation of the filamentous fungal protoplasts is preferably performed in the individual wells of a multiwell plate. Preparation of the protoplasts is not necessarily automated, but can be performed in bulk quantity so that this reagent is available for automated pipetting in robotic transformation method.

The filamentous fungal cell may be any filamentous fungal cell suitable for expression of the polypeptide of interest. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a preferred aspect, the filamentous fungal cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thiela via, Tolypocladium, Trametes,* or *Trichoderma* cell.

In a more preferred aspect, the filamentous fungal cell is an *Aspergillus awamori, Aspergillus fumigatus, Aspergillus foetidus, Aspergillus japonicus, Aspergillus nidulans, Aspergillus niger* or *Aspergillus oryzae* cell. In another more preferred aspect, the filamentous fungal cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another more preferred aspect, the filamentous fungal cell is a *Trichoderma harzianum, Trichoderma koningii, Trichoderma longibrachiatum, Trichoderma reesei*, or *Trichoderma viride* cell. In another more preferred aspect, the filamentous fungal cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Cordolus hirsutus, Humicola insolens, Humicola lanuginosa, Mucor miehei, Myceliophthora thermophila, Neurospora crassa, Penicllium purpurogenum, Phanerochaete chrysosporium, Phlebia radiata, Pleurotus eryngii, Thielavia terrestris, Trametes villosa*, or *Trametes versicolor* cell.

In a most preferred aspect, the filamentous fungal cell is an *Aspergillus oryzae* or *Trichoderma reesei* fungal cell.

Filamentous fungal cells may generally be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787.

In the methods of the present invention, each well containing DNA prepared from a single *E. coli* colony contains a homogenous population of plasmid. Thus, each fungal transformant resulting from transformation of DNA in a single well comprises a single polynucleotide from the DNA library. It is well known in the art that transformation of a DNA library into *E. coli* results in the partitioning of unique plasmids during the stages of replication and cellular division into daughter cells through stochastic processes over the course of a few generations of bacterial growth.

Growth of Filamentous Fungal Transformants and Measurement of Expression or Property In the methods of the present invention, growth of the individual filamentous fungal transformants of step (c) is on a selective medium. The selective growth medium can be added to each transformant contained in individual wells of a multiwell plate. Alternatively, the transformants of step (c) may be transferred to another multiwell plate containing selective growth media. Moreover, the transformants of step (c) can be transferred to a solid-phase selective medium contained in individual wells of a multiwell plate. However, any format known in the art may be used. Nutrients and/or toxic components in the selective medium assure that the transformed fungal cells grow preferentially compared to untransformed cells. The growth medium preferably consists of components that induce expression of the polypeptide of interest. Suitable media are available from commercial suppliers or may be prepared according to published compositions (e.g., in catalogues of the American Type Culture Collection).

The addition of a selective medium, or the transfer of transformants may be performed manually, but is preferably performed by automation. Devices for automation are available commercially, such as a Span-8 pipetting tool of a Beckman Biomek® Fx Robot (Beckman Coulter, Inc., Fullerton, Calif.), a 96-well pipetting head of a liquid handling robot, or a re-arraying tool such as that found on a QBot (Genetix, Limited, Hampshire, UK).

In the methods of the present invention, the step of measuring activity or a property of each polypeptide encoded by the individual polynucleotides is accomplished using methods known in the art that are specific for the polypeptide of interest. These detection methods include, but are not limited to, use of specific antibodies, formation of an enzyme product, or disappearance of an enzyme substrate. Properties include, but are not limited to, altered temperature-dependent activity profile, thermostability, pH activity, pH stability, substrate specificity, product specificity, and chemical stability. The measurement of expression of the polypeptide or a property of the polypeptide encoded by each of the single polynucleotides may be accomplished manually or by automation.

In a preferred aspect, measurement of activity or a property is automated. Any device that allows for automation may be used, e.g., robotic devices. Commercially available devices include, but are not limited to, Biomek® Fx liquid handling robot (Beckman Coulter, Inc., Fullerton, Calif.), Beckman Sagian ORCA® plate handling robotic arm (Beckman Coulter, Inc., Fullerton, Calif.), Caliper SciClone ALH300 Work Station (Caliper Life Sciences, Hopkinton, Mass.), and QBot (Genetix Limited, Hampshire, UK). In order to increase the number of individual activity assays performed in a given time, the activity is conveniently assayed in a high-throughput screening system using multiwell plates. Multiwell plates include, but are not limited to, 96-well MJ Research Hard-Shell® microplates, (MJ Research, Waltham, Mass.), Costar-3370 96-well clear polystyrene plate (Corning, Acton, Mass.), Polypropylene Ultra Rigid Deep-Well Plate (ABgene, Rochester, N.Y.), Costar-3950 1536-well assay plates (Corning, Acton, Mass.), Costar-3706 384-well clear bottom polystyrene plates (Corning, Acton, Mass.), and Costar 24-well cell culture cluster (Corning, Acton, Mass.). Such screening techniques are well known in the art, see, e.g., Taylor et al., 2002, *J. Biomolec. Screening* 7: 554-569; Decker et al., 2003, *Appl. Biochem. Biotech.* 105-108: 689-703; Dove, 1999, *Nature Biotech.* 17: 859-863, and Kell, 1999, *Trends in Biotechnology* 17: 89-91.

Polynucleotides

The methods of the present invention further comprise isolating from one or more of the individual transformants a polynucleotide originating from a DNA library, wherein the polynucleotide encodes a polypeptide of interest. Alternatively, a polynucleotide can be retrieved from the archive DNA library.

The techniques used to isolate or clone a polynucleotide encoding a polypeptide are known in the art and include isolation from genomic DNA, preparation from cDNA, or a combination thereof. The cloning of a polynucleotide from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used.

The polynucleotide may also be a subsequence where one or more nucleotides are deleted from the 5' and/or 3' end of an isolated polynucleotide, wherein the subsequence encodes a polypeptide fragment having biological activity.

Nucleic Acid Constructs

The present invention also relates to nucleic acid constructs comprising an insert or an isolated polynucleotide operably linked to one or more control sequences which direct the expression of the coding sequence in a suitable host cell under conditions compatible with the control sequences.

An isolated polynucleotide (or insert) encoding a polypeptide of interest may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, which is recognized by a filamentous fungal host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacs), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a filamentous fungal host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by a filamentous fungal host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Rhizomucor miehei* aspartic proteinase and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising an isolated polynucleotide or insert, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome, as described herein.

Examples of origins of replication useful in a bacterial or filamentous fungal cell are described herein. Examples of origins of replication for use in a yeast host cell are the 2 micron origin of replication, ARS1, ARS4, the combination of ARS1 and CEN3, and the combination of ARS4 and CEN6.

More than one copy of a polynucleotide may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide isolated according to the present invention or an insert, which are advantageously used in the recombinant production of a polypeptide of interest. A vector comprising an isolated polynucleotide or insert is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausi, Bacillus coagulans, Bacillus lautus, Bacillus lentus, Bacillus licheniformis, Bacillus megaterium, Bacillus stearothermophilus, Bacillus subtilis*, and *Bacillus thuringiensis*, or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, for example, Young and Spizizen, 1961, *Journal of Bacteriology* 81: 823-829, or Dubnau and Davidoff-Abelson, 1971, *Journal of Molecular Biology* 56: 209-221), electroporation (see, for example, Shigekawa and Dower, 1988, *Biotechniques* 6: 742-751), or conjugation (see, for example, Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell, as described herein.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a host cell, as described herein, under conditions conducive for production of the polypeptide; and (b) recovering the polypeptide.

In the production methods of the present invention, the host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

The present invention is further described by the following examples which should not be construed as limiting the scope of the invention.

EXAMPLES

Materials

Chemicals used as buffers and substrates were commercial products of at least reagent grade.

Strains

*Trichoderma reesei* RutC30 strain (ATCC 56765) was used as the source of the cellobiohydrolase I (Cel7A) gene.

*Aspergillus oyrzae* Jal250 (WO99/61651) was used for expression of the *Trichoderma reesei* cellobiohydrolase I (Cel7A).

Media and Solutions

YT medium was composed per liter of 5 g of NaCl, 8 g of tryptone, and 5 g of yeast extract.

YT agar plates were composed per liter of 10 g of agar, 5 g of NaCl, 8 g of tryptone, and 5 g of yeast extract.

2XYT medium was composed per liter of 16 g of tryptone, 10 g of yeast extract, and 5 g of sodium chloride.

2XYT agar medium was composed per liter of 16 g of tryptone, 10 g of yeast extract, 5 g of sodium chloride, and 15 g of Bacto agar.

YP medium was composed per liter of 10 g of yeast extract and 20 g of Bacto peptone.

STC was composed of 0.8 M sorbitol, 25 mM Tris pH 8, and 25 mM $CaCl_2$.

M400 medium was composed per liter of 50 g of maltodextrin, 2 g of $MgSO_4.7H_2O$, 2 g of $KH_2PO_4$, 4 g of citric acid, 8 g of yeast extract, 2 g of urea, 0.5 g of $CaCl_2$, and 0.5 ml of AMG trace metals solution.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

LB medium was composed per liter of 10 g of tryptone, 5 g of yeast extract, and 5 g of NaCl.

STC was composed of 1 M sorbitol, 10 mM $CaCl_2$, and 10 mM Tris-Cl.

TAE buffer was composed per liter of 4.84 g of Tris Base, 1.14 ml of glacial acetic acid, and 2 ml of 0.5 M EDTA pH 8.0.

Example 1

Fermentation and Mycelial Tissue

*Trichoderma reesei* RutC30 was grown under cellulose-inducing standard conditions as described in the art (Mandels and Weber, 1969, *Adv. Chem. Ser.* 95: 391-413). Mycelial samples were harvested by filtration through Whatman paper and quick-frozen in liquid nitrogen. The samples were stored at −80° C. until they were disrupted for RNA extraction.

Example 2

Expressed Sequence Tags (EST) cDNA Library Construction

Total cellular RNA was extracted from the mycelial samples described in Example 1 according to the method of Timberlake and Barnard (1981, *Cell* 26: 29-37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 μg of poly(A)+ mRNA according to the method of Gubler and Hoffman (1983, *Gene* 25: 263-269), except a Not I-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

Bam HI/Eco RI adaptors were ligated to the blunt ends of the cDNA. After digestion with Not I, the cDNA was size selected (ca. 0.7-4.5 kb) by 0.7% agarose gel electrophoresis using TAE buffer, and ligated with pYES2 (Invitrogen Corporation, Carlsbad, Calif.) which had been cleaved with Not I plus Bam HI and dephosphorylated with calf-intestine alkaline phosphatase (Boehringer Mannheim Corporation, Indianapolis, Ind.). The ligation mixture was used to transform competent *E. coli* TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) supplemented with ampicillin at a final concentration of 50 μg per ml.

Example 3

Template Preparation and Nucleotide Sequencing of cDNA Clones

From the cDNA library described in Example 2, approximately 7000 transformant colonies were picked directly from the transformation plates into 96-well microtiter plates in which each well contained 100 μl of 2YT broth supplemented with 50 μg of ampicillin per ml. The plates were incubated overnight at 37° C. with shaking at 200 rpm. After incubation, 100 μl of sterile 50% glycerol was added to each well. The transformants were replicated into secondary, deep-well 96-well plates (Advanced Genetic Technologies Corporation, Gaithersburg, Md.) containing 1 ml of Magnificent Broth™ (MaCconnell Research, San Diego, Calif.) supplemented with 50 μg of ampicillin per ml in each well. The primary microtiter plates were stored frozen at −80° C. The secondary deep-well plates were incubated at 37° C. overnight with vigorous agitation (300 rpm) on a rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter plate cover.

DNA was isolated from each well using a 96-well Miniprep Kit protocol of Advanced Genetic Technologies Corporation (Gaithersburg, Md.) as modified by Utterback et al. (1995, *Genome Sci. Technol.* 1:1-8). Single-pass DNA sequencing (EST) was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and the T7 sequencing primer: T7: 5'-TAATACGACTCACTATAGGG-3' (SEQ ID NO: 1)

Example 4

Analysis of DNA Sequence Data of cDNA Clones

Nucleotide sequence data were scrutinized for quality and vector sequences and ambiguous base calls at the ends of the DNA sequences were trimmed, and all sequences were compared to each other with assistance of PHRED/PHRAP software (University of Washington, Seattle, Wash.). The resulting contigs and singletons were translated in six frames and searched against publicly available protein databases using GeneMatcher™ software (Paracel, Inc., Pasadena, Calif.) with a modified Smith-Waterman algorithm using the BLOSUM 62 matrix.

Example 5

Identification of a cDNA Clone Encoding a Family 7 Cellobiohydrolase I (Cel7A)

Putative cDNA clones encoding a Family 7 cellobiohydrolase (Cel7A) were identified by comparing the deduced amino acid sequence of the assembled ESTs to protein sequences deposited in publicly available databases such as Swissprot, Genpept, and PIR. One clone, *Trichoderma reesei* EST Tr0221, was selected for nucleotide sequence analysis which revealed an 1821 bp pYES2 insert which contained a 1452 bp open reading-frame as shown in SEQ ID NO: 2 and a deduced amino acid sequence as shown in SEQ ID NO: 3. The plasmid containing *Trichoderma reesei* Cel7A cellobiohydrolase I gene was designated pTr0221. Plasmid pAJO52 contained in *E. coli* NRRL B-30683 can also be used as a source of the gene.

Example 6

Construction of pAlLo2 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using Big-Dye™ terminator chemistry as described. Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis.) according to the manufacturer's instructions using the following primers (underlined nucleotide represents the changed base):

AMDS3NcoMut (2050):
5'-GTGCCCCATGA̲TACGCCTCCGG-3'    (SEQ ID NO: 4)

AMDS2NcoMut (2721):
5'-GAGTCGTATTTCCAA̲GGCTCCTGACC-3'    (SEQ ID NO: 5)

AMDS1NcoMut (3396):
5'-GGAGGCCATGA̲AGTGGACCAACGG-3'    (SEQ ID NO: 6)

A plasmid comprising all three expected sequence changes was then submitted to site-directed mutagenesis, using a QuickChange™ Site-Directed Mutagenesis Kit (Stratagene, La Jolla, Calif.), to eliminate the Nco I restriction site at the end of the AMG terminator at position 1643. The following primers (underlined nucleotide represents the changed base) were used for mutagenesis:
Upper Primer to Mutagenize the AMG Terminator Sequence:

5'-CACCGTGAAAGCCATGC̲TCTTTCCTTCGTGTA    (SEQ ID NO: 7)
GAAGACCAGACAG-3'

Lower Primer to Mutagenize the AMG Terminator Sequence:

5'-CTGGTCTTCTACACGAAGGAAAGAG̲CATGGCT    (SEQ ID NO: 8)
TTCACGGTGTCTG-3'

The last step in the modification of pBANe6 was the addition of a new Nco I restriction site at the beginning of the polylinker using a QuickChange™ Site-Directed Mutagenesis Kit and the following primers (underlined nucleotides represent the changed bases) to yield pAlLo1 (FIG. 1).
Upper Primer to Mutagenize the NA2-tpi Promoter:

(SEQ ID NO: 9)
5'-CTATATACACAACTGGATTTACC̲ATGGGCCCGCGGCCGCAGATC-3'

Lower Primer to Mutagenize the NA2-tpi Promoter:

(SEQ ID NO: 10)
5'-GATCTGCGGCCGCGGGCCCATGGTAAATCCAGTTGTGTATATAG-3'

Figure 2:
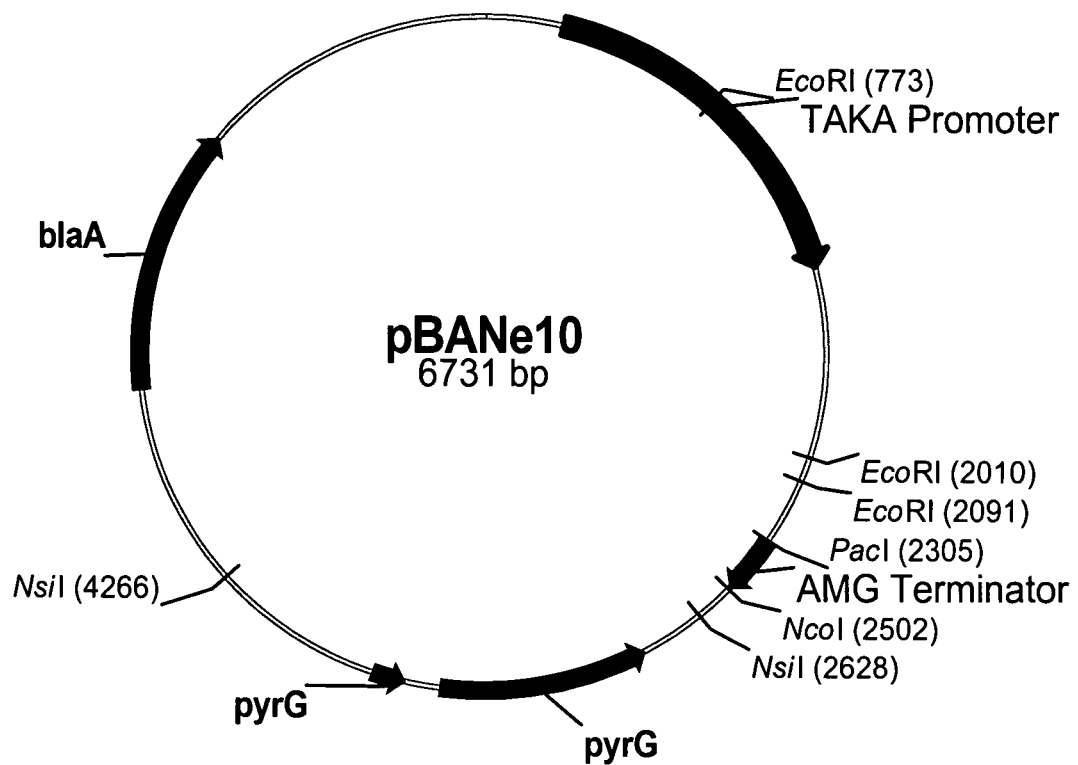
FIG. 2 shows a restriction map of pBANe10.
Figure 3:
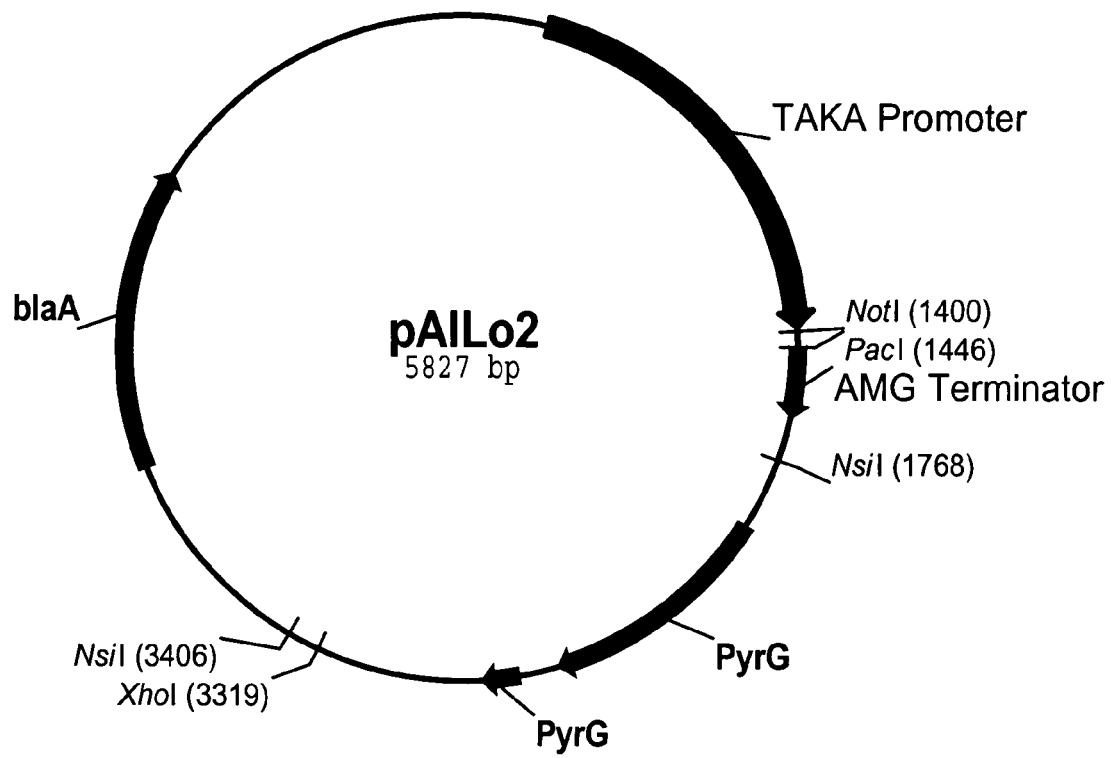
FIG. 3 shows a restriction map of pAlLo2.

The amdS gene of pAlLo1 was swapped with the *Aspergillus nidulans* pyrG gene. Plasmid pBANe10 (FIG. 2) was used as a source for the pyrG gene as a selection marker. Analysis of the sequence of pBANe10 showed that the pyrG marker was contained within an Nsi I restriction fragment and does not contain either NCO I or Pac I restriction sites. Since the amdS is also flanked by Nsi I restriction sites the strategy to switch the selection marker was a simple swap of Nsi I restriction fragments. Plasmid DNA from pAlLo1 and pBANe10 were digested with the restriction enzyme Nsi I and the products purified by agarose gel electrophoresis. The Nsi I fragment from pBANe10 containing the pyrG gene was ligated to the backbone of pAlLo1 to replace the original Nsi I DNA fragment containing the amdS gene. Recombinant clones were analyzed by restriction digest to determine that they had the correct insert and also its orientation. A clone with the pyrG gene transcribed in the counterclockwise direction was selected. The new plasmid was designated pAlLo2 (FIG. 3).

Example 7

Construction of pCW026

Subcloning of the Cel7A cellobiohydrolase I gene into pAlLo2 was accomplished by designing two primers, shown below, that allowed cloning into the Nco I and Pac I sites.

Primer cTR0221.7 incorporates a BspLU II site, which is compatible to the Nco I site in pAlLo2, to the 5'-end of the Cel7A cellobiohydrolase I gene. Primer cTR0221.7a incorporates a Bsp LUII site at the 3'-end of the Cel7A cellobiohydrolase I gene.

```
                                          (SEQ ID NO: 11)
Primer cTR0221.7:   5'-GCAACATGTATCGGAAGTTGGC-3'

(SEQ ID NO: 12)
Primer cTR0221.7a:  5'-AATTAATTTTACAGGCACTGAG-3'
```

Amplification of the Cel7A cellobiohydrolase I gene was accomplished using 1× Tgo Polymerase Reaction buffer (Boehringer Mannheim Co, Indianapolis, Ind.), 25 ng of pTR0221, 0.2 mM each of dATP, dGTP, dCTP, and dTTP, 50 pmole of each primer (cTR0221.7 and cTR0221.7a), and 1 unit of Tgo polymerase (Boehringer Mannheim Co, Indianapolis, Ind.). The reactions were incubated using a MJ Research Thermocycler (MJ Research, Inc., Boston, Mass.) programmed for one cycle at 95° C. for 5 minutes, followed by 35 cycles each at 94° C. for 60 seconds, 55° C. for 45 seconds, and 72° C. for 2 minutes. The reactions were then incubated at 72° C. for a 5 minute extension. An aliquot of each PCR product was run on a 0.7% agarose gel using TAE buffer generating expected bands of approximately 1545 bp.

Figure 4:
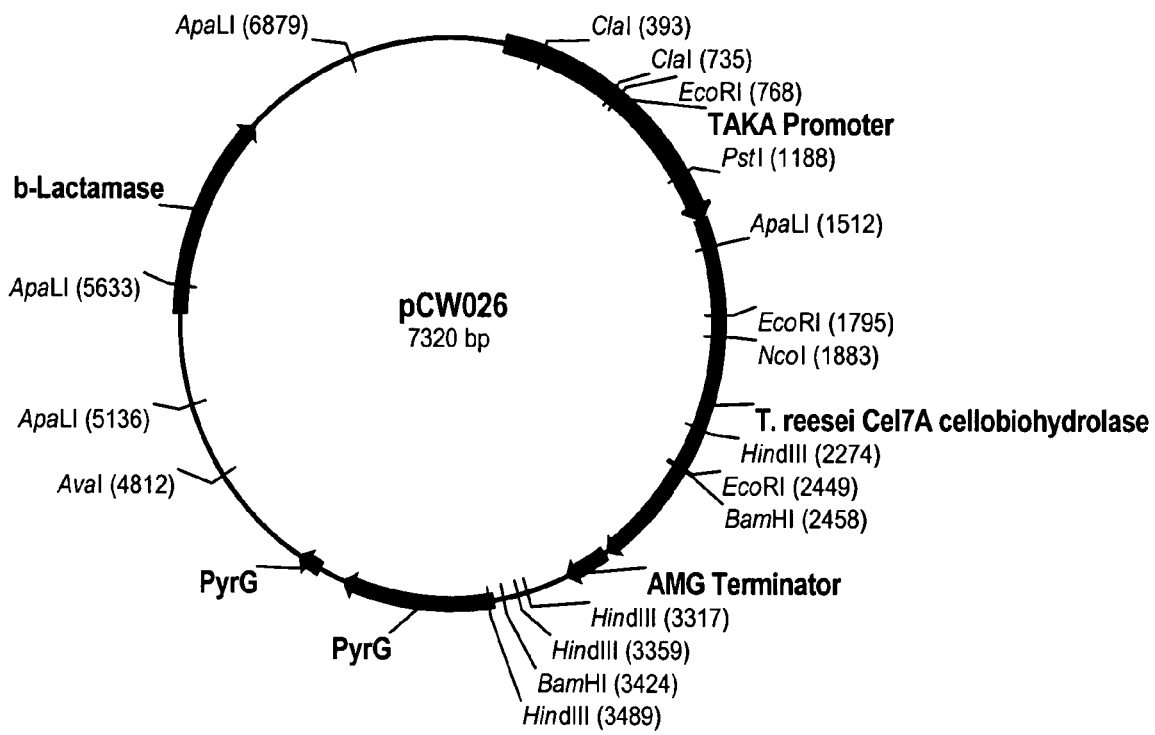
FIG. 4 shows a restriction map of pCW026.

The 1545 bp PCR product was subcloned using a Zero Blunt® TOPO® PCR Cloning Kit (Invitrogen, Carlsbad, Calif.). The resulting plasmid was digested with Bsp LUII and Pac I and fractionated on a 0.7% agarose gel using TAE buffer generating an expected 1.5 kb coding sequence, which was excised and gel purified using an Amicon® Ultra-free DA column (Millipore, Billerica, Mass.). The resulting fragment was subsequently ligated into pAlLo2, which was similarly digested, to generate the expression vector designated pCW026 (FIG. 4) containing the *Trichoderma reesei* Cel7A cellobiohydrolase I gene.

Example 8

Construction of Plasmid pENi2229

In order to improve expression of a gene of interest on an expression plasmid, it may be desirable to reduce the expression of the gene marker used for selection, exemplified here by the pyrG gene. By cultivating a host cell harbouring an expression plasmid comprising a selection gene that has reduced expression, under normal selective pressure, this results in selection for a host cell which has an increased plasmid copy number, thus achieving the total expression level of the selection gene necessary for survival. The higher plasmid copy-number, however, also results in an increased expression of the gene of interest.

One way of decreasing the expression level of the selection gene is to lower the mRNA level by either using a poorly transcribed promoter or decreasing the functional half-life of the mRNA. Another way is to reduce translation efficiency of the mRNA. One way to do this is to mutate the Kozak-region (Kozak, 1999, *Gene* 234: 187-208). This is a region just upstream of the initiation codon (ATG), which is important for the initiation of translation. The following section describes construction of an expression vector containing state of the art promoter and terminator elements, and a disrupted Kozak-region upstream of a selection gene.

pMT2188. Plasmid pMT2188 was based on the *Aspergillus* expression plasmid pCaHj483 (WO 98/00529), which consists of an expression cassette based on the *Aspergillus niger* neutral amylase II promoter fused to the *Aspergillus nidulans* triose phosphate isomerase non translated leader sequence (NA2-tpi) and the *Aspergillus niger* amyloglycosidase terminator (AMG). Also present on the pCaHj483 is the *Aspergillus* selective marker amdS from *Aspergillus nidulans* enabling growth on acetamide as the sole nitrogen source. These elements were cloned into the *E. coli* vector pUC19 (New England Biolabs, Beverly, Mass.). The ampicillin resistance marker enabling selection in *E. coli* of pUC19 was replaced with the URA3 marker of *Saccharomyces cerevisiae* that can complement a pyrF mutation in *E. coli*, the replacement was performed as described below. The pUC19 origin of replication was PCR amplified from pCaHj483 with the primers shown below:

```
                                          (SEQ ID NO: 13)
142779:   5'-TTGAATTGAAAATAGATTGATTTAAAACTTC-3'

(SEQ ID NO: 14)
142780:   5'-TTGCATGCGTAATCATGGTCATAGC-3'
```

Primer 142780 introduces a Bbu I site in the PCR fragment. The Expand™ PCR system (Roche Molecular Biochemicals, Basel, Switzerland) was used for the amplification, following the manufacturers instructions for this and the subsequent PCR amplifications.

The URA3 gene was amplified from the general *Saccharomyces cerevisiae* cloning vector pYES2 (Invitrogen corporation, Carlsbad, Calif., USA) using the primers:

```
                                          (SEQ ID NO: 15)
140288:   5'-TTGAATTCATGGGTAATAACTGATAT-3'

(SEQ ID NO: 16)
142778:   5'-AAATCAATCTATTTTCAATTCAATTCATCATT-3'
```

Primer 140288 introduces an Eco RI site in the PCR fragment. The two PCR fragments were fused by mixing them and amplifying using the primers 142780 (SEQ ID NO: 14) and 140288 (SEQ ID NO: 15) in the splicing by overlap method (Horton et al., 1989, *Gene* 77: 61-68).

The resulting fragment was digested with Eco RI and Bbu I and ligated to the largest fragment of pCaHj483 digested with the same enzymes. The ligation mixture was used to transform the pyrF *E. coli* strain DB6507 (ATCC 35673) made competent by the method of Mandel and Higa (1970, *J. Mol. Biol.* 45: 154). Transformants were selected on solid M9 medium (Sambrook et al, 1989, *Molecular Cloning, a Laboratory Manual*, 2nd edition, Cold Spring Harbor Laboratory Press) supplemented with 1 g/l casamino acids, 500 microgram/l thiamine and 10 mg/l kanamycin.

A plasmid from a selected transformant was termed pCaHj527. The NA2-tpi promoter present on pCaHj527 was subjected to site directed mutagenesis by a simple PCR approach. Nucleotides 134-144 were altered from GTAC-TAAAACC to CCGTTAAATTT using the mutagenic primer 141223 (SEQ ID NO: 17). Nucleotides 423-436 were altered from ATGCAATTTAAACT to CGGCAATTTAACGG using the mutagenic primer 141222 (SEQ ID NO: 17). The resulting plasmid was termed pMT2188.

```
                                          (SEQ ID NO: 17)
141223:   5'-GGATGCTGTTGACTCCGGAAATTTAACGGTTTGGTCTTG
          CATCCC-3'

(SEQ ID NO: 18)
141222:   5'-GGTATTGTCCTGCAGACGGCAATTTAACGGCTTCTGCGA
          ATCGC-3'
``` pENI1849. Plasmid pENI1849 was made in order to truncate the pyrG gene, to eliminate non-essential sequences for pyrG expression, in order to decrease the size of the plasmid, allowing for optimal transformation frequency. A PCR fragment (approx. 1800 bp) was made using pENI1299 (WO 00/24883) as template and the primers below. The Expand™ PCR system was used for the amplification following the manufacturer's instructions.

```
270999J8:
5'-TCTGTGAGGCCTATGGATCTCAGAAC-3'    (SEQ ID NO: 19)

270999J9:
5'-GATGCTGCATGCACAACTGCACCTCAG-3'   (SEQ ID NO: 20)
```

The PCR-fragment was digested with the restriction enzymes Stu I and Sph I, and cloned into pENI1298 (disclosed in WO 00/24883), also digested with Stu I and Sph I. The cloning was verified by sequencing.

pENI1861. Plasmid pENI1861 was constructed to include a state of the art *Aspergillus* promoter, as well as a number of unique restriction sites for cloning. A PCR fragment (approx. 620 bp) was amplified using plasmid pMT2188 as the template with the primers below. The Expand™ PCR system was used for the amplification following the manufacturer's instructions.

```
051199J1:
                                    (SEQ ID NO: 21)
5'-CCTCTAGATCTCGAGCTCGGTCACCGGTGGCCTCCGCGGCCGCTGGA
TCCCCAGTTGTG-3'

1298-TAKA:
                                    (SEQ ID NO: 22)
5'-GCAAGCGCGCGCAATACATGGTGTTTTGATCAT-3'
```

The fragment was digested with BssH II and Bgl II, and cloned into pENI1849 which was also digested with BssHII and BglII. The cloning was verified by sequencing.

pENI2151. Plasmids pENI1902 (described in WO 2002/059331) and pENI1861 were each digested with Hind III. Both a 2408 bp fragment from pENI1861 and the digested vector pENI1902 were purified from a 1.0% agarose gel using TAE buffer, excised from the gel, and purified using a QIAquick® Gel Extraction Kit following the manufacturer's instructions.

The fragment and the vector were ligated using T4 DNA ligase (Roche Molecular Biochemicals, Basel, Switzerland) following the manufacturer's instructions, and transformed into the *E. coli* strain DH10B™ (Invitrogen, Carlsbad, Calif.). A plasmid from one of the transformants was isolated using a Qiaprep® Miniprep Kit, and it was designated pENI2151.

pENI2155. Plasmid pENI2155 was constructed to disrupt the Kozak region upstream of the pyrG gene. Using pENI1861 as template two PCR reactions were run. Primers 141200J1 (below) and 270999J9 (SEQ ID NO: 20) were used in one PCR reaction, and primers 141200J2 (below) and 290999J8 (SEQ ID NO: 19) in another PCR reaction.

```
                                    (SEQ ID NO: 23)
141200J1: 5'-ATCGGTTTTATGTCTTCCAAGTCGCAATTG-3'

(SEQ ID NO: 24)
141200J2: 5'-CTTGGAAGACATAAAACCGATGGAGGGGTAGCG-3'
```

The Expand™ PCR System was used for the amplifications, following the manufacturer's instructions. The resulting fragments were resolved on a 1.0% agarose gel using TAE buffer, excised from the gel, and purified using a QIAquick® Gel Extraction Kit, according the instructions included with the kit.

Another PCR-reaction was run using the above mentioned fragments as template along with the primers 270999J8 (SEQ ID NO: 19) and 270999J9 (SEQ ID NO: 20). The Expand™ PCR system was used for the amplification following the manufacturer's instructions. The PCR fragment from this reaction was resolved on a 1.0% agarose gel using TAE buffer, excised from the gel, and purified using a QIAquick® Gel Extraction Kit following the manufacturer's instructions.

The fragment and the pENI1849 were digested with Stu I and Sph I. The resulting fragments were purified from a 1.0% agarose gel as above. The purified fragments were ligated using T4 DNA ligase, and transformed into *E. coli* strain DH10B™ (Invitrogen, Carlsbad, Calif.) according to the manufacturer's instructions. Plasmid DNA from one of the transformants was isolated using a Qiaprep® Miniprep Kit and sequenced to confirm the introduction of the mutated Kozak region, shown below:

```
5'-GGTTTTATG-3'      (SEQ ID NO: 25)
```

The wild type Kokak that has been replaced is below:

```
5'-GCCAACATG-'3      (SEQ ID NO: 26)
```

This plasmid was designated pENI2155.

pENI2207. Plasmids pENI2151 and pENI2155 were digested with Stu I and Sph I. Both the 2004 bp fragment from pENI2155 and digested vector pENI2151 were purified from a 1.0% agarose gel using TAE buffer, excised from the gel, and purified using a QIAquick® Gel Extraction Kit following the manufacturer's instructions.

The fragment and the vector were ligated, and transformed into *E. coli* strain DH10B™ according to the manufacturer's instructions. Plasmid from one of the transformants was isolated using a Qiaprep® Miniprep Kit and designated pENI2207.

pENI2229. Using pENI2151 as template and PWO polymerase (Roche Applied Science, Indianapolis, Ind.) following the manufacturer's instructions, a PCR reaction was performed using primer 2120201J1 and 1298-TAKA.

```
1298-TAKA:
                                    (SEQ ID NO: 27)
5'-GCAAGCGCGCGCAATACATGGTGTTTTGATCAT-3'

2120201J1:
                                    (SEQ ID NO: 28)
5'-GCCTCTAGATCTCCCGGGCGCCGGCACATGTACCAGGTCTTAAGCTC
GAGCTCGGTCACCGGTGGCC-3'
```

The resulting 650 bp PCR fragment was purified from a 1.0% agarose gel, excised from the gel, and purified using a QIAquick® Gel Extraction Kit following the manufacturer's instructions.

Figure 5:
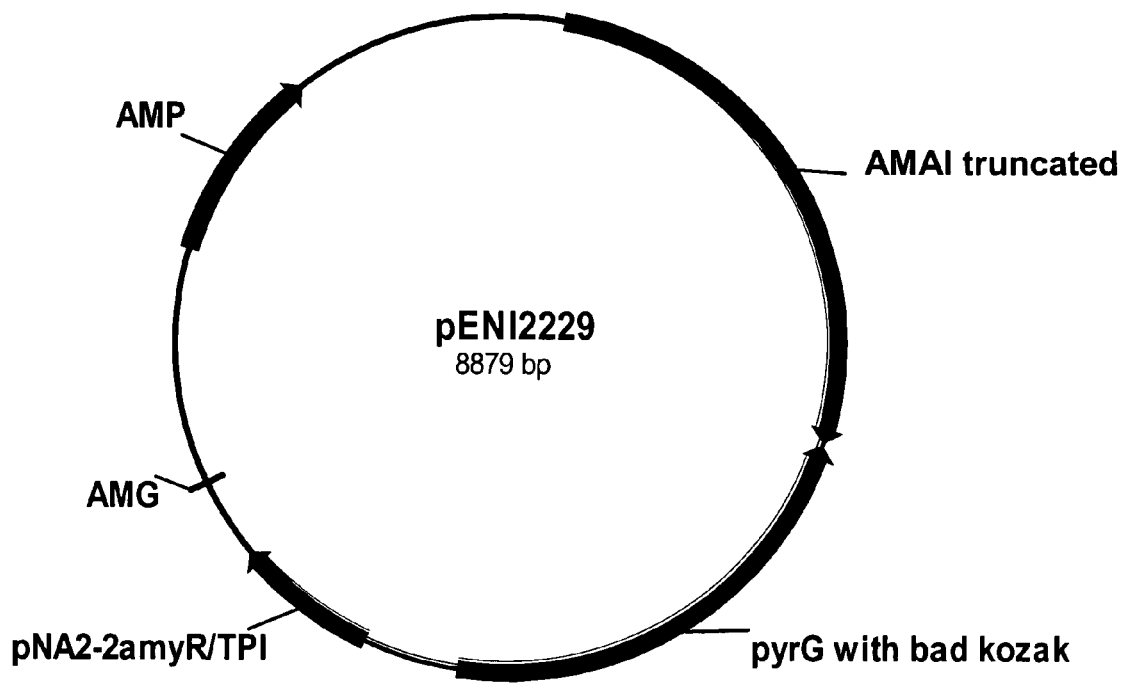
FIG. 5 shows a restriction map of pENI2229.

The PCR fragment (650 bp) and pENI2207 were digested with Bss HII and Bgl II. The vector and the PCR fragment were purified from a 1.0% agarose gel using QIAGEN™ spin columns following the manufacturer's instructions. The PCR fragment and digested vector were ligated using T4 DNA ligase, and transformed into *E. coli* strain DH10B™ (Invitrogen, Carlsbad, Calif.) according to the manufacturer's instructions. Plasmid from one of the transformants was isolated using a Qiaprep® Miniprep Kit, verified by DNA sequencing, and designated pENi2229 (FIG. 5).

Example 9

Construction of pCW013

Plasmid pCW013 was constructed from pENi2229 to obtain expression of a *Humicola insolens* cellobiohydrolase I in *Aspergillus oryzae*. The coding sequence for *Humicola insolens* cellobiohydrolase I was amplified by PCR from pHD459b, as described by Dalboge and Heldt-Hansen, 1994, *Mol. Gen. Gene* 243: 253-260.

The PCR fragment containing the full-length cellobiohydrolase I gene was subcloned into pENi2229 as a Bam HI/Xma I fragment. Construction of pCW013 was accomplished as described below.

PCR fragments were extended with a Bam HI site on the 5' end of the cellobiohydrolase I gene and an Xma I site on the 3' end using the following primers.

```
                                       (SEQ ID NO: 29)
Primer 1: 5'-CGCGGATCCACCATGCGTACCGCCAAGTTCGCC-3'

(SEQ ID NO: 30)
Primer 2: 5'-GCCCCGGGTTACAGGCACTGAGAGTACCAG-3'
```

The amplification reactions (50 µl) contained the following components: 0.3 µg of pHD459b, 1 unit of PWO polymerase, 1× PWO polymerase buffer, 0.2 mM dNTPs, 50 pmol of primer 1, and 50 pmol of primer 2. The reactions were incubated in an Eppendorf Mastercycler® (Eppendorf, Westbury, N.Y.) programmed for 30 cycles each at 95° C. for 30 seconds, 55° C. for 30 seconds and 72° C. for 1 minute.

The reaction products were then resolved on a 0.8% agarose gel using TAE buffer and a 1605 bp product band was excised from the gel and purified using an Amicon Ultrafree® DA Centrifugal Unit (Millipore, Bedford, Mass.) according to manufacturer's instructions. The purified product was then ligated and transformed using a Zero Blunt® TOPO® PCR Cloning Kit (Invitrogen, Carlsbad, Calif.) following the manufacturer's instructions. The transformation was plated on 2XYT agar medium supplemented with 100 µg of ampicillin per liter and grown overnight at 37° C.

White colonies were picked into 3 ml of 2XYT medium supplemented with 100 µg of ampicillin per liter and grown overnight at 37° C. Plasmid DNA was isolated from the cultures using a QIAGEN® Qiabot® Miniprep Station (QIAGEN Inc., Valencia, Calif.) following the manufacturer's instructions. The plasmid DNA was analyzed by restriction mapping with Bam HI and Xma I to identify clones positive for insertion of the cellobiohydrolase I gene. Once a clone was validated for successful insertion of the cellobiohydrolase I gene, the clone was sequenced for fidelity using BigDye Terminator Version 3 and analyzed using an ABI PRISM® 3700 DNA Analyzer (Foster City, Calif.) according the manufacturer's instructions.

An *E. coli* TOPO clone containing the cellobiohydrolase I gene was digested with Bam HI and Xma I and the fragment was then resolved on a 0.8% agarose gel using TAE buffer and a 1605 bp fragment was excised and purified using an Amicon Ultrafree® DA Centrifugal Unit (Amicon, Beverly, Mass.) following the manufacturer's instructions.

Plasmid pENi2229 was digested in the same manner with Bam HI and Xma I to create compatible ends to the 1605 bp cellobiohydrolase I fragment. The pENi2229 digestion product was resolved on a 0.8% agarose gel using TAE buffer and an 8810 bp fragment was excised and purified using an Amicon Ultrafree® DA Centrifugal Unit according to the manufacturer's instructions.

Figure 6:
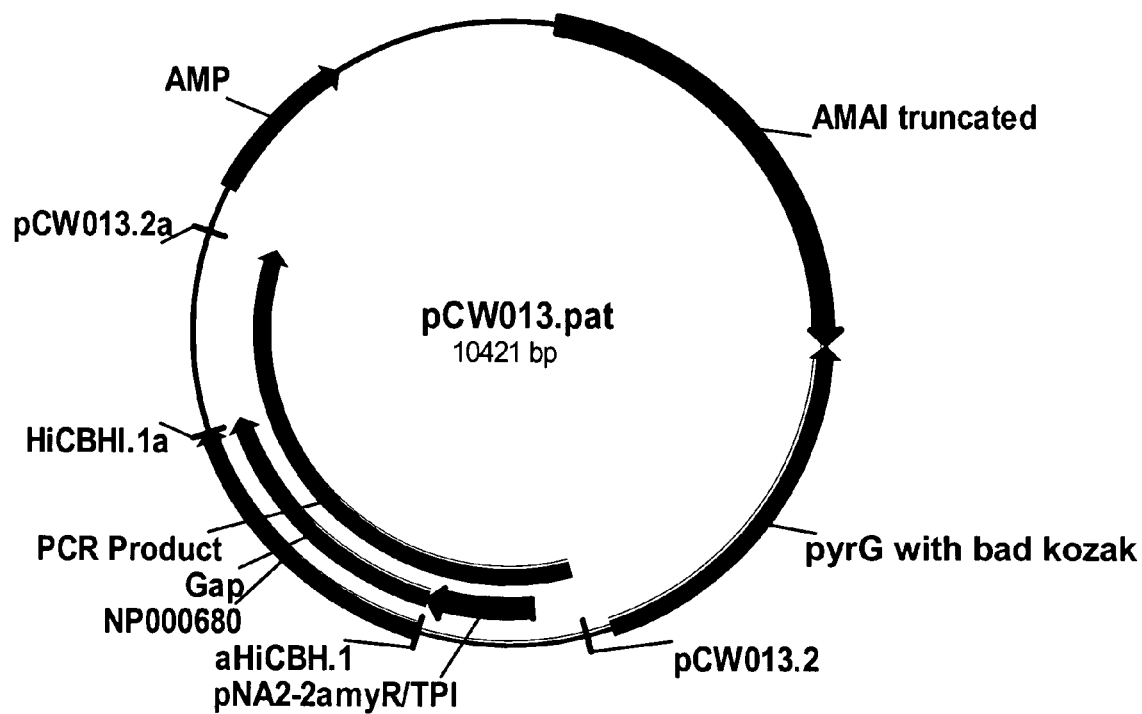
FIG. 6 shows a restriction map of pCW013.

The Bam HI/Xma I cellobiohydrolase I gene fragment was ligated into Bam HI/Xma I digested pENi2229 using a Rapid DNA Ligation Kit (Roche, Indianapolis, Ind.) following the manufacturer's instructions. This ligation was then used to transform *E. coli* Sure® Cells Stratagene, La Jolla, Calif.) following the manufacturer's instructions. Colonies were selected, cultured, and plasmid was prepared as described above. The plasmid DNA was analyzed by restriction mapping using Bam HI and Xma I to identify clones positive for insertion of the cellobiohydrolase I gene. One plasmid isolated from a positive colony was designated pCW013 (FIG. 6).

Example 10

Small Volume Transformation of Plasmid DNA, with Selection of Transformants in the Same Tube Protoplasts of *Aspergillus oryzae* Jal250 were prepared by first inoculating 100 ml of YP medium supplemented with 2% glucose with approximately $2-5 \times 10^7$ spores. The spores were prepared by growth of *Aspergillus oryzae* Jal250 for 16-18 hours at 34° C., 140 rpm in YP medium supplemented with 2% glucose and 10 mM uridine. Mycelia were collected using a sterile vacuum filter to remove the medium. The mycelial mat was washed 3 times by re-suspending the mat with 100 ml of 0.7 M KCl and vacuum filtering. Finally, the mat was re-suspended in 20 ml of protoplasting solution and transferred to a 125 ml flask that was incubated at 34° C., 80 rpm. The protoplasting solution was composed of 5 mg/ml Glucanex (Novozymes A/S, Bagsvaerd, Denmark), 0.5 mg/ml Chitinase (Sigma, St. Louis, Mo.), and 0.7 M KCl. Protoplasts began to release between 30 and 90 minutes. The protoplasts were filtered through a sterile funnel lined with Miracloth™ (Calbiochem, La Jolla, Calif.) into a 50 ml polypropylene tube, which was then centrifuged at 600×g for 10 minutes at room temperature using a Sorvall RT 6000D centrifuge (E. I. DuPont De Nemours and Co., Wilmington, Del.). The pellet was then re-suspended in STC, washed twice with 20 ml of STC, and centrifuged at 2000 rpm as above for 10 minutes to pellet the protoplasts. The protoplasts were counted using a hemocytometer and re-suspended in STC to a final concentration of $2 \times 10^7$ protoplasts/ml. The protoplasts were stored at −80° C., after controlled-rate freezing in a Nalgene® 5100 Cryo 1° C. Freezing Container, "Mr. Frosty" (VWR Scientific, Inc., San Francisco, Calif.).

The protoplasts were used to perform single well transformations using the following method. First, 15 microliters of *Aspergillus oryzae* Jal250 protoplasts and 1 µg of circular pCW026 DNA were aliquoted into 48 wells of a 96-well deep-well plate (QIAGEN Inc., Valencia, Calif.). Two controls were also used in this experiment. Eight wells contained protoplasts but no DNA as a control to ascertain that untransformed protoplasts could not grow in the M400 medium and to allow detection of possible cross-contamination from the successful transformants. In addition, eight wells contained pCW013 as a positive control for transformation. The transformation efficiency of the AMA plasmid is known to be about 100-fold higher than for integrating plasmids (Osheroy and May, 2000, *Genetics* 155: 647-656). Following addition of DNA to the protoplasts, 50 µl of 60% PEG, 10 mM Tris, and 10 mM $CaCl_2$ was added to each well and the plate was sealed with a QIAGEN© Airpore Tape Sheet (QIAGEN Inc., Valencia, Calif.), placed in a zip loc bag, and incubated at 37°

C. for 25 minutes. After incubation, 200 µl of STC was added to each well, followed by addition of 400 µl of M400 medium. The plate was once again sealed with a QIAGEN© Airpore Tape Sheet (QIAGEN Inc., Valencia, Calif.), placed in a zip loc bag, and incubated at 34° C. for 6 days.

After incubation, positive transformants were selected based on their ability to grow in M400 medium as a selective medium for transformants. Positive transformants have the ability to produce uridine which allows them to cultivate in selective media. As described above, 400 µl of M400 medium was added directly to each well where transformation took place. Positive transformants were detected by the formation of mycelial mats. The broth from those wells positive for growth was then removed and assayed for cellobiohydrolase I expression.

Example 11

High-Throughput Assay for Expression of the Cellobiohydrolase I Transgene

Broths were directly sampled from the 96-well transformation 96-well deep-well plate of Example 10 into a standard 96-well plate. The broths from each well were assayed for activity on the cellobiohydrolase I substrate 4-methyl-beta-D-umbelliferyl lactoside (MUL). The methyl-ubelliferyl group fluoresces when the lactose moiety is cleaved by a cellobiohydrolase. As a control, a broth from an *Aspergillus oryzae* transformant generated using the empty cloning vector was used. In addition, a broth containing cellobiohydrolase I obtained from a shake flask culture of the cellobiohydrolase I transformant was run as an additional positive control.

Thirty microliters of *Aspergillus oryzae* broth was assayed by addition of 30 µl of 0.25 mg/ml MUL in 100 mM succinate, pH 5.0, 0.01% Tween-20. Duplicate reactions were assayed at 50° C. The reactions were run for 45 minutes and then quenched by addition of 1.5 M Tris-Cl pH 9.5. Fluorescence was measured using a BMG FLUOStar Galaxy fluorometer (Offenburg, Germany) (excitation 360 nm, emission 460 nm). Activity from the vector-only transformant broth was subtracted from activity of test wells.

On day 6, 65% (31 of 48) of the wells that contained the integrating plasmid pCW026 in the transformation reaction contained fungal mats. Of these 31 transformants, only four had produced visible spores by day 6. The eight control wells where no DNA was added had no fungal mats on day 6. All eight of the transformations with the AMA plasmid developed fungal mats by day 6.

Four of 31 transformants generated by single-well transformation with the integrating plasmid showed cellobiohydrolase I activity when assayed on MUL. The four transformants that expressed cellobiohydrolase I were the same four colonies which had grown sufficiently by day 6 to produce spores.

Example 12

Automated Sampling of Broth from Fungal Cultures Grown in 96-Well V-Bottom Titer Plates For small volume assays, cultures can be grown in 96-titer plates (120 µl broth) that have a V-shaped bottom (for example, Costar Thermowell® series titer plates, Corning, Acton, Mass., or MJ Research Hard-Shell® microplates, MJ Research, Waltham, Mass., for example.) *Aspergillus oryzae* JaL250 cultures were grown for 5-10 days at 34° C. in M400 medium. Using a 96-well pippetting tool of a Biomek® Fx Robot (Beckman Coulter, Inc, Fullerton, Calif.), the mycelial wells could be depressed in the wells. Due to the V-shape of the wells, the mycelia gets stuck in the bottom of the plate. The broth was displaced to the top of the well. From these wells, broth was then removed without clogging the tips with hyphae.

Example 13

Automated Inoculation of 24-Well Plate from 96-Well Plate Spores

Inoculation of the wells of 24-well multiwell plates (Costar 24 well cell culture cluster, Corning, Acton, Mass.) from 96-well multiwell plates was performed using a Biomek® Fx Robot Span-8 pipetting tool (Beckman Coulter, Inc, Fullerton, Calif.). One hundred and twenty microliters of sterile water was deposited onto the surface of *Aspergillus oryzae* JaL250 mycelial mats that had grown in 96-well multiwell plates (100 µl volume, grown at 34° C. for 5-14 days) as described in Example 10. Mixing was performed by pipetting to loosen the spores present on top of the growth mats. One hundred microliters of spores from each well was transferred to wells of a 24-well plate containing 1.5 ml of fresh M400 culture medium. The 24-well plates were incubated at 34° C. for 4-10 days.

Example 14

Automated Sampling of Culture Broth from Fungal Cultures Grown in a 24-Well Format A Biomek® Fx Robot (Beckman Coulter, Inc, Fullerton, Calif.) was used to remove 200 µl of broth from each well of the 24-well culture plate of Example 13, and the 200 µl samples were transferred to a 96-well plate (Hard-Shell® 96-well multiwell plates, MJ Research, Waltham, Mass.). The Span-8 pipetting tool of the Beckman Biomek® Fx Robot was used to move aside the fungal mat, which grew at the surface of the broth. Briefly, the tip drags the mycelial mat to one side of the well so that the broth can be removed.

This method was found to reliably displace mycelial mats so that broth was pipetted accurately from the well without clogging of the tip from mycelial mats. Up to 1 ml of total broth could be removed from these cultures.

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| E. coli pAJO52 | NRRL B-30683 | Jul. 29, 2003 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for expression screening of filamentous fungal transformants, comprising:
   (a) isolating single colony transformants of a DNA library of different plasmids introduced into *E. coli*, wherein each different plasmid comprises a different polynucleotide encoding a different polypeptide operably linked to control sequences for expression and secretion of each different polypeptide in a filamentous fungus;
   (b) preparing each different plasmid from each of the single colony *E. coli* transformants, wherein each single colony comprises a different plasmid comprising a different polynucleotide from the DNA library;
   (c) introducing a sample of each of the different plasmid preparations of step (b) into separate suspensions of protoplasts of a filamentous fungus to obtain transformants thereof, wherein each transformant contains one or more copies of an individual and different plasmid from the DNA library;
   (d) growing the individual filamentous fungal transformants obtained from transformation of each of the different plasmid preparations of step (c) on growth medium that selects for filamentous fungal transformants, while suppressing growth of untransformed filamentous fungi, and also enables expression and secretion of each different polypeptide into the growth medium; and
   (e) measuring activity or a property of each different polypeptide encoded by each individual and different DNA secreted into the culture medium of step (d).

2. The method of claim 1, wherein the DNA library is a library of mutants of a gene.

3. The method of claim 2, wherein the mutated genes encode polypeptide variants.

4. The method of claim 1, wherein the polypeptide encoded by the polynucleotide is an antibody, antigen, enzyme, hormone, or reporter.

5. The method of claim 4, wherein the enzyme is selected from the group consisting of an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinase, peptidoglutaminase, peroxidase, phytase, polyphenoloxidase, protease, ribonuclease, transglutaminase, and xylanase.

6. The method of claim 1, wherein the polypeptide is a variant.

7. The method of claim 1, wherein the filamentous fungus is selected from the group consisting of an *Acremonium, Aspergillus, Fusarium, Humicola, Mucor, Myceliophthora, Neurospora, Penicillium, Thielavia, Tolypocladium*, and *Trichoderma* strain.

8. The method of claim 1, further comprising (f) isolating a polynucleotide originating from the DNA library, wherein the polynucleotide encodes a polypeptide of interest.

9. The method of claim 1, wherein one or more steps are automated.

10. The method of claim 1, wherein each step is automated.

11. An isolated polynucleotide encoding a polypeptide of interest obtained by the method of claim 8.

12. A nucleic acid construct comprising the polynucleotide of claim 11.

13. A recombinant expression vector comprising the polynucleotide of claim 11.

14. A recombinant host cell comprising the polynucleotide of claim 11.

* * * * *